(12) United States Patent
Turner et al.

(10) Patent No.: US 7,994,160 B2
(45) Date of Patent: Aug. 9, 2011

(54) PYRIDAZINE COMPOUNDS AS GLYCOGEN SYNTHASE KINASE 3 INHIBITORS

(75) Inventors: Sean C. Turner, Mannheim (DE); Margaretha Bakker, Ludwigshafen (DE); Roland Grandel, Dossenheim (DE); Michael Vierling, Ludwigshafen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 222 days.

(21) Appl. No.: 11/988,578

(22) PCT Filed: Jul. 12, 2006

(86) PCT No.: PCT/EP2006/006826
§ 371 (c)(1),
(2), (4) Date: May 12, 2009

(87) PCT Pub. No.: WO2007/006566
PCT Pub. Date: Jan. 18, 2007

(65) Prior Publication Data
US 2009/0325937 A1 Dec. 31, 2009

Related U.S. Application Data

(60) Provisional application No. 60/698,647, filed on Jul. 12, 2005.

(51) Int. Cl.
C07D 487/04 (2006.01)
C07D 471/14 (2006.01)
A61K 31/55 (2006.01)
A61K 31/551 (2006.01)

(52) U.S. Cl. ......... 514/211.04; 514/211.05; 514/211.06; 514/220; 514/221; 540/488; 540/490; 540/495; 540/502

(58) Field of Classification Search .................. 540/488, 540/490, 495, 502; 514/211.04, 211.05, 514/211.06, 220, 221
See application file for complete search history.

(56) References Cited

U.S. PATENT DOCUMENTS
7,232,814 B2 6/2007 Meijer et al.

FOREIGN PATENT DOCUMENTS
WO WO 01/60374 8/2001

OTHER PUBLICATIONS

Ott, Ingo et al., "Substituted Pyridazino[3,4-b][1,5]benzoxapin-5(6H)on es as Multidrug-Resistance Modulating Agents" Journal of Medicinal Chemistry, 47(18), 4627-4630 CODEN: JMCMAR; ISSN: 0022-2623, 2004 XP002406965.
Heinisch et al., "Synthesis of Substituted Tri- and Tetracyclic Compounds Bearing a Pyridazine Core and their Biological Evaluation as Anitmycobacterial Agents" Arch. Phar. Pharm. Med. Chem., vol. 333, 2000, pp. 231-240, XP009074716.
Heinisch et al., "Pyridazines. 81. A novel 1,2-diazine containing tricyclic system: synthesis of pyridazinol[3,4-b][1,5]benzodiazepin-5-ones as potential HIV-1 reverse transcriptase inhibitors", Heterocycles, 45(4), pp. 673-682 CODEN: HTCYAM; ISSN: 0385-5414, 1997, XP001248027.
Heinisch et al., "Synthesis of Pyridazino[3,4-b][1,5]benzodiazepin-5-ones and their Biological Evaluation as Non-nucleoside HIV Reverse Transcriptase Inhibitors" Arch. Pharm. Pharm. Med. Chem., vol. 330, 1997, pp. 29-34, XP009074715.
Barth et al., "Pyridazino[3,4-b][1,5]benzoxazepin-5(6H)-ones: synthesis and biological evaluation" Antiviral Chemistry and Chemotherapy, 7(6), pp. 300-312 CODEN: ACCHEH; ISSN: 0956-3202, 1996, XP009074718.
Tavares et al., "N-Phenyl-4-pyrazolo[1,5-b]pyridazin-3ylpy rimidin-2-amines as Potent and Selective Inhibitors of Glycogen Synthase Kinase 3 with Good Cellular Efficacy" J. Med. Chem., vol. 47, 2004, pp. 4716-4730, XP002406982.

Primary Examiner — Bruck Kifle
(74) Attorney, Agent, or Firm — Lisa V. Mueller; Polsinelli Shughart PC

(57) ABSTRACT

Disclosed are pyridazine compounds of the formula I which are useful for inhibiting glycogen synthase kinase 3 (GSK-3), methods of making the compounds, compositions containing the compounds, and methods of treatment using the compounds:

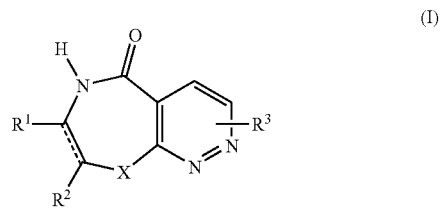

(I)

In formula I ---- indicates a single bond or a double bond;
X is O, S or N—$R^5$;
$R^1$, $R^2$ are independently selected from the group consisting of H, $NH_2$, NH—$C_1$-$C_6$-alkyl, OH, =O, (i.e. a carbonyl group), $C_1$-$C_6$-alkoxy, halogen, methyl, $C_2$-$C_4$-alkyl, $C_3$-$C_4$-cycloalkyl, $C_3$-$C_4$-alkenyl, fluorinated $C_1$-$C_4$-alkyl, fluorinated $C_3$-$C_4$-cycloalkyl, fluorinated $C_3$-$C_4$-alkenyl, formyl, $C_1$-$C_3$-alkylcarbonyl, and an aromatic radical Ar,
$R^1$ and $R^2$ together with the carbon atoms, to which they are attached, form a fused, saturated or unsaturated 5-, 6- or 7-membered C-bound carbocyclic or heterocyclic ring comprising 1 heteroatom, selected from nitrogen, oxygen and sulfur as ring member and 0, 1 or 2 further heteroatoms, independently selected from O, S and N, as ring members, wherein the fused ring is unsubstituted or may carry 1, 2 or 3 substituents selected, independently of each other, from the group of radicals $R^4$ as defined below;
$R^3$ is hydrogen OH, halogen, CN, nitro, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, fluorinated $C_2$-$C_6$-alkenyl, $C_2$-$C_6$-alkynyl, $C_3$-$C_7$-cycloalkyl, fluorinated $C_3$-$C_7$-cycloalkyl, $C_1$-$C_6$-alkoxy, $C_1$-$C_6$-hydroxyalkoxy, $C_1$-$C_6$-alkoxy-$C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, carboxy, $C_1$-$C_6$-alkyloxycarbonyl, fluorinated $C_1$-$C_6$-alkoxycarbonyl, $NR^aR^b$, C(O)—$NR^eR^f$, NH—C(O)—$NR^eR^f$, $NR^aR^b$—$C_1$-$C_6$-alkylene, O—$NR^aR^b$, etc.
and wherein $R^4$ and $R^5$ are as defined in the specification and the claims.

16 Claims, No Drawings

PYRIDAZINE COMPOUNDS AS GLYCOGEN SYNTHASE KINASE 3 INHIBITORS

CROSS-REFERENCE TO RELATED APPLICATIONS

This is the U.S. National Stage entry of International Patent Application No. PCT/EP2006/006826, filed on Jul. 12, 2006, which claims priority to U.S. Provisional Patent Application No. 60/698,647, filed on Jul. 12, 2005, the contents of all of which are hereby incorporated by reference.

TECHNICAL FIELD

The present invention relates to novel pyridazine compounds which are useful for inhibiting glycogen synthase kinase 3 (GSK-3), methods of making the compounds, compositions containing the compounds, and methods of treatment using the compounds.

BACKGROUND OF THE INVENTION

Glycogen synthase kinase-3 (GSK-3) is a serine/threonine kinase encoded by two isoforms, GSK-3α and GSK-3β with molecular weights of 51 and 47 kDa, respectively. These share 97% sequence similarity in their kinase catalytic domains. The GSK-3α isoform has an extended glycine-rich N-terminal tail. A minor splice variant of GSK-3β has been identified (expressed at ~15% of total) with a 13 amino acid insert within the kinase domain. This variant had a reduced activity towards tau. GSK-3 is highly conserved throughout evolution, and found in all mammalians thus far with high homology in the kinase domain. Both isoforms are ubiquitously expressed in mammalian tissues, including the brain. Pharmacological GSK-3 inhibitors are not able to selectively inhibit one of the isoforms.

GSK-3β plays an important role in the control of metabolism, differentiation and survival. It was initially identified as an enzyme able to phosphorylate and hence inhibit glycogen synthase. Subsequently, it was recognised that GSK-3β was identical to tau protein kinase 1 (TPK1), an enzyme that phosphorylates tau protein in epitopes that are also found to be hyperphosphorylated in Alzheimer's disease and in several taupathies.

Interestingly, protein kinase B (AKT) phosphorylation of GSK-3β results in a loss of kinase activity, and it has been proposed that this inhibition may mediate some of the effects of neurotrophic factors. Moreover, phosphorylation of β-catenin (a protein involved in cell survival) by GSK-3β, results in its degradation by an ubiquitinilation dependent proteasome pathway.

Therefore it appears that inhibition of GSK-3β activity may result in neurotrophic activity. There is evidence that lithium, an uncompetitive inhibitor of GSK-3β, enhances neuritogenesis in some models and can also increase neuronal survival, through the induction of survival factors such as Bcl-2 and the inhibition of the expression of proapoptotic factors such as P53 and Bax.

Further studies have shown that β-amyloid increases GSK-3β activity and tau protein phosphorylation. Moreover, this hyperphosphorylation as well as the neurotoxic effects of β-amyloid are blocked by lithium chloride and by a GSK-3β antisense mRNA. These observations taken together suggest that GSK-3β may be the link between the two major pathological processes in Alzheimer's disease: abnormal APP (Amyloid Precursor Protein) processing and tau protein hyperphosphorylation.

These experimental observations indicate that compounds which modulate the GSK-3β activity may find application in the treatment of the neuropathological consequences and the cognitive and attention deficits associated with Alzheimer's disease, as well as other acute and chronic neurodegenerative diseases. These include, but are not limited to: Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma.

GSK-3β may also have utility in the treatment of other diseases such as: Non-insulin dependent diabetes and obesity; manic depressive illness; schizophrenia; alopecia; cancers such as breast cancer, non-small cell lung carcinoma, thyroid cancer, T or B-cell leukemia and several virus-induced tumors.

B. Barth et al. (Antiviral Chemistry & Chemotherapy 7 (6), 1996, 300-312) describe 6-alkyl substituted pyridazino[3,4-b][1,5]benzoxazepin-5-ones which are useful as inhibitors of HIV-1 reverse transcriptase. They also describe several pyridazino[3,4-b][1,5]benzoxazepin-5(6H)-ones being unsubstituted at the nitrogen as intermediates, namely pyridazino[3,4-b][1,5]benzoxazepin-5(6H)-one, 3-chloropyridazinobenzo[3,4-b][1,5]benzoxazepin-5(6H)-one, 3-chloro-8-trifluoromethylpyridazino[3,4-b][1,5]benzoxazepin-5(6H)-one, 3-chloro-8-methylpyridazino[3,4-b][1,5]benzoxazepin-5(6H)-one, 3-chloro-9-methylpyridazino[3,4-b][1,5]benzoxazepin-5(6H)-one, 3-chloro-8-methoxypyridazino[3,4-b][1,5]benzoxazepin-5(6H)-one and 3-chloro-8,10-dimethylpyridazinobenzo[3,4-b][1,5]benzoxazepin-5(6H)-one.

G. Heinisch et al. (Arch. Pharm. Pharm. Med. Chem. 2000, 333, 231-240) describe pyridazinobenzo[3,4-b][1,5]benzoxazepin-5(6H)-ones being unsubstituted at the nitrogen as intermediates in the synthesis of the corresponding N-alkyl derivatives, namely 3-chloropyridazinobenzo[3,4-b][1,5]benzoxazepin-5(6H)-one, 3,8-dichloropyridazino[3,4-b][1,5]benzoxazepin-5(6H)-one, 3-chloro-8-methylpyridazino[3,4-b][1,5]benzoxazepin-5(6H)-one and 3-chloro-9-methylpyridazino[3,4-b][1,5]benzoxazepin-5(6H)-one.

I. Ott et al. (J. Med. Chem. 2004, 47, 4627-4630) describe 6-alkyl substituted pyridazinobenzo[3,4-b][1,5]benzoxazepin-5-ones which are useful as Multidrug-Resistance Modulating agents in tumor therapy. They also describe several pyridazinobenzo[3,4-b][1,5]benzoxazepin-5(6H)-ones being unsubstituted at the nitrogen as intermediates, e.g. 3-chloro-9-trifluoromethylpyridazino[3,4-b][1,5]benzoxazepin-5(6H)-one.

G. Heinisch et al. (Arch. Pharm. Pharm. Med. Chem. 1997, 330, S. 29-34 and Heterocycles 1997, 45, 673-682) describe inter alia 3-chloro-8-nitro-11-propylpyridazino[3,4-b][1,5]benzodiazipin-5-one.

SUMMARY OF THE INVENTION

The object of the present invention is to provide compounds which modulate the GSK-3β activity, in particular compounds which have an inhibitory activity on GSK-3β and which thus are useful as an active ingredient of a composition for preventive and/or therapeutic treatment of a disease caused by abnormal GSK-3β activity, especially of neurodegenerative diseases. More specifically, the goal is to provide novel compounds useful as an active ingredient of a composition that enables prevention and/or treatment of neurodegenerative diseases such as Alzheimer's disease.

It was surprisingly found that certain polycyclic pyridazine compound of the general formula I as defined herein have the desired activity and thus are useful as an active ingredient of a composition that enables prevention and/or treatment of the aforementioned diseases. Therefore the present invention relates to a method for treatment of a disease caused by abnormal GSK-3β activity, which method comprises administering at least one compound of the formula I or a physiologically tolerated acid addition salts thereof as described herein to a subject in need thereof:

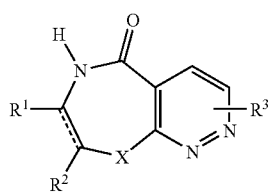

(I)

and its physiologically tolerated acid addition salts, wherein
- - - - indicates a single bond or a double bond;

X is O, S or N—$R^5$;

$R^1$, $R^2$ are independently selected from the group consisting of H, $NH_2$, NH—$C_1$-$C_6$-alkyl, OH, =O, (i.e. a carbonyl group), $C_1$-$C_6$-alkoxy, halogen, methyl, $C_2$-$C_4$-alkyl, $C_3$-$C_4$-cycloalkyl, $C_3$-$C_4$-alkenyl, fluorinated $C_1$-$C_4$-alkyl, fluorinated $C_3$-$C_4$-cycloalkyl, fluorinated $C_3$-$C_4$-alkenyl, formyl, $C_1$-$C_3$-alkylcarbonyl, and an aromatic radical Ar, which is selected from the group consisting of phenyl and a 5- or 6-membered C-bound heteroaromatic radical, comprising 1 nitrogen atom as ring member and 0, 1, 2 or 3 further heteroatoms, independently selected from O, S and N, as ring members, wherein Ar is unsubstituted or carries 1 radical $R^{1a}$ or, $R^1$ and $R^2$ together with the carbon atoms, to which they are attached, form a fused, saturated or unsaturated 5-, 6- or 7-membered C-bound carbocyclic or heterocyclic ring comprising 1 heteroatom, selected from nitrogen, oxygen and sulfur as ring member and 0, 1 or 2 further heteroatoms, independently selected from O, S and N, as ring members, wherein the fused ring is unsubstituted or may carry 1, 2 or 3 substituents selected, independently of each other, from the group of radicals $R^4$ as defined below;

$R^3$ is selected from the group consisting of H, OH, halogen, CN, nitro, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, fluorinated $C_2$-$C_6$-alkenyl, $C_2$-$C_6$-alkynyl, $C_3$-$C_7$-cycloalkyl, fluorinated $C_3$-$C_7$-cycloalkyl, $C_1$-$C_6$-alkoxy, $C_1$-$C_6$-hydroxyalkoxy, $C_1$-$C_6$-alkoxy-$C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, carboxy, $C_1$-$C_6$-alkyloxycarbonyl, fluorinated $C_1$-$C_6$-alkoxycarbonyl, $NR^aR^b$, C(O)—$NR^eR^f$, NH—C(O)—$NR^eR^f$, $NR^aR^b$—$C_1$-$C_6$-alkylene, O—$NR^aR^b$, phenylsulfonyl, benzyloxy, phenoxy, where the phenyl radical in the 3 last-mentioned radicals may be unsubstituted or may carry 1, 2 or 3 substituents selected, independently of each other, from the group of radicals $R^{3a}$, phenyl and a 5- or 6-membered C- or N-bound heteroaromatic radical comprising 1 nitrogen atom as ring member and 0, 1, 2 or 3 further heteroatoms independently selected from O, S and N, as ring members, wherein phenyl and the heteroaromatic radical are, independently of each other, unsubstituted or carry 1, 2 or 3 substituents selected, independently of each other, from the group of radicals $R^{3b}$;

$R^4$ is selected from the group consisting of OH, halogen, CN, nitro, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, fluorinated $C_2$-$C_6$-alkenyl, $C_3$-$C_7$-cycloalkyl, fluorinated $C_3$-$C_6$-cycloalkyl, $C_1$-$C_6$-alkoxy, $C_1$-$C_6$-hydroxyalkoxy, $C_1$-$C_6$-alkoxy-$C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, carboxy, $C_1$-$C_6$-alkyloxycarbonyl, fluorinated $C_1$-$C_6$-alkoxycarbonyl, $NR^aR^b$, C(O)—$NR^eR^f$, NH—C(O)—$NR^eR^f$, $NR^aR^b$—$C_1$-$C_6$-alkylene, O—$NR^aR^b$, phenylsulfonyl, benzyloxy, phenoxy, where the phenyl radical in the 3 last-mentioned radicals may be unsubstituted or may carry 1, 2 or 3 substituents selected, independently of each other, from the group of radicals $R^{4a}$, phenyl and a 5- or 6-membered C- or N-bound heteroaromatic radical comprising 1 nitrogen atom as ring member and 0, 1, 2 or 3 further heteroatoms independently selected from O, S and N, as ring members, wherein phenyl and the heteroaromatic radical are, independently of each other, unsubstituted or carry 1, 2 or 3 substituents selected, independently of each other, from the group of radicals $R^{4b}$;

$R^5$ is selected from the group consisting of H, $C_1$-$C_6$-alkyl, $C_2$-$C_6$-alkenyl, C(O)—$R^c$, C(O)—$OR^d$, C(O)—$NR^eR^f$; and wherein $R^{1a}$ is selected from the group consisting of halogen, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $NR^eR^f$, 1-aziridinyl, azetidin-1-yl, pyrrolidin-1-yl, piperidin-1-yl, morpholin-4-yl and homopiperidin-1-yl, a phenyl group or an aromatic 5- or 6-membered C-bound heteroaromatic radical comprising 1 nitrogen atom as ring member and 0, 1, 2 or 3 further heteroatoms independently selected from O, S and N, as ring members, wherein phenyl and the heteroaromatic radical are, independently of each other, unsubstituted or substituted by 1, 2, 3 or 4 radicals selected from halogen, cyano, $C_1$-$C_4$-alkyl, fluorinated $C_1$-$C_4$-alkyl, $C_1$-$C_4$-alkoxy and fluorinated $C_1$-$C_4$-alkoxy;

$R^{3a}$, $R^{4a}$ are independently selected from the group consisting of halogen, CN, nitro, OH, $C_1$-$C_4$-alkyl, fluorinated $C_1$-$C_4$-alkyl, $C_1$-$C_4$-alkoxy and fluorinated $C_1$-$C_4$-alkoxy $C_1$-$C_4$-alkylcarbonyl, fluorinated $C_1$-$C_4$-alkylcarbonyl, $C_1$-$C_4$-alkylcarbonylamino, fluorinated $C_1$-$C_4$-alkylcarbonylamino, carboxy, $C_1$-$C_6$-alkyloxycarbonyl, fluorinated $C_1$-$C_6$-alkoxycarbonyl, C(O)—$NR^eR^f$, NH—C(O)—$NR^eR^f$, $NR^aR^b$, $NR^aR^b$—$C_1$-$C_6$-alkylene, O—$NR^aR^b$, $R^{3b}$, $R^{4b}$ are independently selected from the group consisting of halogen, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $NR^eR^f$, 1-aziridinyl, azetidin-1-yl, pyrrolidin-1-yl, piperidin-1-yl, piperazin-1-yl, morpholin-4-yl and homopiperidin-1-yl, a phenyl group or an aromatic 5- or 6-membered C-bound heteroaromatic radical comprising 1 nitrogen atom as ring member and 0, 1, 2 or 3 further heteroatoms independently selected from O, S and N, as ring members, wherein phenyl and the heteroaromatic radical are, independently of each other, unsubstituted or substituted by 1, 2, 3 or 4 radicals selected from halogen, cyano, $C_1$-$C_4$-alkyl, fluorinated $C_1$-$C_4$-alkyl, $C_1$-$C_4$-alkoxy and fluorinated $C_1$-$C_4$-alkoxy;

$R^a$, $R^b$ are independently selected from the group consisting of H, $C_1$-$C_4$-alkyl, fluorinated $C_1$-$C_4$-alkyl or $C_1$-$C_4$-alkoxy or may form, together with N, a 4-, 5-, 6- or 7-membered saturated or unsaturated N-heterocyclic ring, which may carry 1 further heteroatom, selected from O, S and N as a ring member;

$R^c$ is selected from the group consisting of hydrogen, $C_1$-$C_6$-alkyl, $C_3$-$C_6$-cycloalkyl, fluorinated $C_1$-$C_6$-alkyl, fluorinated $C_3$-$C_6$-cycloalkyl, phenyl wherein phenyl is unsubstituted or substituted by 1, 2, 3 or 4 radicals selected from halogen, cyano, $C_1$-$C_4$-alkyl, fluorinated $C_1$-$C_4$-alkyl, $C_1$-$C_4$-alkoxy and fluorinated $C_1$-$C_4$-alkoxy;

$R^d$ is $C_1$-$C_6$-alkyl, $C_3$-$C_6$-cycloalkyl, fluorinated $C_1$-$C_6$-alkyl, fluorinated $C_3$-$C_6$-cycloalkyl, phenyl wherein phenyl is unsubstituted or substituted by 1, 2, 3 or 4 radicals selected from halogen, cyano, $C_1$-$C_4$-alkyl, fluorinated $C_1$-$C_4$-alkyl, $C_1$-$C_4$-alkoxy and fluorinated $C_1$-$C_4$-alkoxy;

$R^e$ and $R^f$ are independently selected from the group consisting of H, $C_1$-$C_4$-alkyl, fluorinated $C_1$-$C_4$-alkyl or $C_1$-$C_4$-alkoxy or may form, together with N, a 4-, 5-, 6- or 7-membered saturated or unsaturated N-heterocyclic ring, which may carry 1 further heteroatom, selected from O, S and N as a ring member.

The compounds of the present invention modulate the activity of GSK-3β. In particular, they have inhibitory activity against GSK-3β. Accordingly, the compounds of the present invention are useful for treatment of a medical disorder susceptible to treatment with a compound that modulates and in particular inhibits glycogen synthase kinase 3β activity.

The polycyclic pyridazine compounds of the general formula I have not yet been described, except for:
pyridazino[3,4-b][1,5]benzoxazepin-5(6H)-one,
3-chloropyridazinobenzo[3,4-b][1,5]benzoxazepin-5(6H)-one (compound of the formula I, wherein X is O, $R^1$ and $R^2$ together form a fused benzene ring and wherein $R^3$ is chlorine which is located in the 3-position (i.e. ortho with regard to the pyridazine nitrogen)), 3,8-dichloropyridazino[3,4-b][1,5]benzoxazepin-5(6H)-one (compound of the formula I, wherein $R^3$ is chlorine, located in the 3-position of the pyridazine ring, X is O, $R^1$ and $R^2$ together form a fused benzene ring which carries a chlorine atom in the 8-positon of the tricyclic core (i.e. para with regard to the carbon atom that is adjacent to X), 3-chloro-8-trifluoromethylpyridazino[3,4-b][1,5]benzoxazepin-5(6H)-one, 3-chloro-9-trifluoromethylpyridazino[3,4-b][1,5]benzoxazepin-5(6H)-one (compound of the formula I, wherein $R^3$ is chlorine, located in the 3-position of the pyridazine ring, X is O, $R^1$ and $R^2$ together form a fused benzene ring which carries a trifluoromethyl group in the 9-positon of the tricyclic core (i.e. para with regard to the carbon atom that is adjacent to X),
3-chloro-8-methylpyridazino[3,4-b][1,5]benzoxazepin-5(6H)-one,
3-chloro-9-methylpyridazino[3,4-b][1,5]benzoxazepin-5(6H)-one,
3-chloro-8-methoxypyridazino[3,4-b][1,5]benzoxazepin-5(6H)-one,
3-chloro-8,10-dimethylpyridazinobenzo[3,4-b][1,5]benzoxazepin-5(6H)-one and 3-Chloro-8-nitro-11-propyl-5H-pyridazino[3,4-b][1,5]benzodiazepin-5-one (compound of the formula I, wherein X is N-propyl, $R^1$ and $R^2$ together form a fused benzene ring which carries a nitro group in the 8-position of the tricyclic core (i.e. para with regard to the common carbon atom that is adjacent to X) and wherein $R^3$ is chlorine which is located in the 3-position (i.e. ortho with regard to the pyridazine nitrogen)).

Therefore the present invention also relates to polycyclic pyridazine compound of the general formula I, and to their pharmacologically acceptable acid addition salts, except for the compounds already known.

The present invention also relates to a pharmaceutical composition which comprises at least one polycyclic pyridazine compound of the formula (I) and/or at least one physiologically tolerated acid addition salt of (I), where appropriate together with physiologically acceptable carriers and/or auxiliary substances.

The present invention in particular relates to a method for treatment of neurodegenerative diseases caused by abnormal activity of GSK-3β and of the aforementioned diseases which comprises administering to a mammalian organism in need thereof an effective amount of a compound of the formula (I).

DETAILED DESCRIPTION OF THE INVENTION

According to the invention, the compounds of the general formula I having the meanings mentioned at the outset have a modulating, and in particular inhibitory activity against GSK-3β. Accordingly, the compounds of the present invention are useful for treatment of a medical disorder susceptible to treatment with a compound that modulates and in particular inhibits glycogen synthase kinase 3β activity. The term "treatment", as used herein includes preventive treatment and therapeutic treatment. Thus, these compounds are useful as an active ingredient for the preparation of a composition, which enables treatment of a disease caused by abnormal GSK-3β activity and more particularly of neurodegenerative diseases such as Alzheimer's disease. In addition, the compounds of the present invention are also useful for treatment of neurodegenerative diseases such as Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma. The compounds are also useful for treatment of other medical disorders susceptible to treatment with a compound that modulates and in particular inhibits glycogen synthase kinase 3β activity, such as non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

Provided the compounds of the formula I of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula I and/or of their salts.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

$C_1$-$C_4$ Alkyl is a straight-chain or branched alkyl group having from 1 to 4 carbon atoms. Examples of an alkyl group are methyl, $C_2$-$C_4$-alkyl such as ethyl, n-propyl, isopropyl, n-butyl, 2-butyl, iso-butyl or tert-butyl. $C_1$-$C_2$ Alkyl is methyl or ethyl, $C_1$-$C_3$ alkyl is additionally n-propyl or isopropyl.

$C_1$-$C_6$ Alkyl is a straight-chain or branched alkyl group having from 1 to 6 carbon atoms. Examples include methyl, $C_2$-$C_4$ alkyl as mentioned above and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Fluorinated $C_1$-$C_6$ alkyl is a straight-chain or branched alkyl group having from 1 to 6, especially 1 to 4 carbon atoms (=fluorinated $C_1$-$C_4$ alkyl), in particular 1 to 3 carbon atoms (=fluorinated $C_1$-$C_3$ alkyl), wherein at least one, e.g. 1, 2, 3, 4 or all of the hydrogen atoms are replaced by a fluorine atom such as in fluoromethyl, difluoromethyl, trifluoromethyl, (R)-1-fluoroethyl, (S)-1-fluoroethyl, 2-fluoroethyl, 1,1-difluoroethyl, 2,2-difluoroethyl, 2,2,2-trifluoroethyl, 1,1,2,2-tetrafluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-(trifluoromethyl)-2,2,2-trifluoroethyl, 1-(trifluoromethyl)-1,2,2,2-tetrafluoroethyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, and the like.

$C_1$-$C_6$ Alkoxy is a straight-chain or branched alkyl group having from 1 to 6, in particular 1 to 4 carbon atoms (=$C_1$-$C_4$ alkoxy), which is bound to the remainder of the molecule via an oxygen atom. Examples include methoxy, ethoxy, n-propoxy, isopropoxy, n-butoxy, 2-butoxy, iso-butoxy, tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Fluorinated $C_1$-$C_6$ alkoxy is a straight-chain or branched alkoxy group having from 1 to 6, in particular 1 to 4 carbon atoms (=fluorinated $C_1$-$C_4$ alkoxy), wherein at least one, e.g. 1, 2, 3, 4 or all of the hydrogen atoms are replaced by a fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1,1,2,2-tetrafluoroethoxy, (R)-1-fluoropropoxy, (S)-1-fluoropropoxy, (R)-2-fluoropropoxy, (S)-2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, and the like.

$C_1$-$C_6$ Hydroxyalkyl is a straight-chain or branched alkyl group having from 1 to 6, especially 1 to 4 carbon atoms (=$C_1$-$C_4$ hydroxyalkyl), in particular 1 to 3 carbon atoms (=$C_1$-$C_3$ hydroxyalkyl), wherein one of the hydrogen atoms is replaced by a hydroxy group, such as in hydroxymethyl, 1- or 2-hydroxyethyl or 1-, 2- or 3-hydroxypropyl.

$C_1$-$C_6$ Hydroxyalkoxy is a straight-chain or branched alkoxy group having from 1 to 6, especially 1 to 4 carbon atoms (=$C_1$-$C_4$ hadroxyalkoxy), in particular 1 to 3 carbon atoms (=$C_1$-$C_3$ hydroxyalkoxy), wherein one of the hydrogen atoms is replaced by a hydroxy group, such as in 2-hydroxyethoxy or 3-hydroxypropyloxy.

$C_1$-$C_6$-Alkoxy-$C_1$-$C_6$-alkyl is a straight-chain or branched alkyl group having from 1 to 6, especially 1 to 4 carbon atoms, in particular 1 to 3 carbon atoms, wherein one of the hydrogen atoms is replaced by a $C_1$-$C_6$-alkoxy group, such as in methoxymethyl, 2-methoxyethyl, ethoxymethyl, 3-methoxypropyl, 3-ethoxypropyl and the like.

$C_1$-$C_6$-Alkoxy-$C_1$-$C_6$-alkoxy is a straight-chain or branched alkyl group having from 1 to 6, especially 1 to 4 carbon atoms, in particular 1 to 3 carbon atoms, wherein one of the hydrogen atoms is replaced by a $C_1$-$C_6$-alkoxy group, such as in 2-methoxyethoxy, ethoxymethoxy, 2-ethoxyethoxy, 3-methoxypropoxy, 3-ethoxypropoxy and the like.

$C_1$-$C_6$-Alkylcarbonyl is a straight-chain or branched alkyl group having from 1 to 6, especially 1 to 4 carbon atoms (=$C_1$-$C_4$ alkylcarbonyl), in particular 1 to 3 carbon atoms (=$C_1$-$C_3$ alkylcarbonyl), which is bound to the remainder of the molecule via a carbonyl group (CO), such as in acetyl and propionyl.

Fluorinated $C_1$-$C_6$-alkylcarbonyl is a straight-chain or branched alkyl group having from 1 to 6, especially 1 to 4 carbon atoms (=fluorinated $C_1$-$C_4$ alkylcarbonyl), in particular 1 to 3 carbon atoms (=fluorinated $C_1$-$C_3$ alkylcarbonyl), which is bound to the remainder of the molecule via a carbonyl group (CO), and wherein at least one of the remaining hydrogen atoms, e.g. 1, 2, 3, or 4 of the hydrogen atoms are replaced by a fluorine atom, such as in trifluoroacetyl and 3,3,3-trifluoropropionyl.

$C_1$-$C_6$-Alkoxycarbonyl is a straight-chain or branched alkoxy group having from 1 to 6, especially 1 to 4 carbon atoms (=$C_1$-$C_4$ alkoxycarbonyl), in particular 1 to 3 carbon atoms (=$C_1$-$C_3$ alkoxycarbonyl), which is bound to the remainder of the molecule via a carbonyl group (CO), such as in methoxycarbonyl, ethoxycarbonyl, propyloxycarbonyl, and isopropyloxycarbonyl.

Fluorinated $C_1$-$C_6$-alkoxycarbonyl is a straight-chain or branched alkoxy group having from 1 to 6, especially 1 to 4 carbon atoms (=fluorinated $C_1$-$C_4$ alkoxycarbonyl), in particular 1 to 3 carbon atoms (=fluorinated $C_1$-$C_3$ alkoxycarbonyl), which is bound to the remainder of the molecule via a carbonyl group (CO), and wherein at least one of the remaining hydrogen atoms, e.g. 1, 2, 3, or 4 of the hydrogen atoms are replaced by a fluorine atom, such as in fluormethoxycarbonyl, trifluoromethoxycarbonyl and 2,2,2-triflourethoxycarbonyl.

$C_1$-$C_6$-Alkylcarbonylamino is a straight-chain or branched alkyl group having from 1 to 6, especially 1 to 4 carbon atoms (=$C_1$-$C_4$ alkylcarbonylamino), in particular 1 to 3 carbon atoms (=$C_1$-$C_4$ alkylcarbonylamino), wherein one of the hydrogen atoms is replaced by a carbonylamino group (CO—NH—), such as in acetamido (acetylamino) ($CH_3CONH$—) and propionamido ($CH_3CH_2CONH$—).

Fluorinated $C_1$-$C_6$-alkylcarbonylamino is a straight-chain or branched alkyl group having from 1 to 6, especially 1 to 4 carbon atoms (=fluorinated $C_1$-$C_4$ alkylcarbonylamino), in particular 1 to 3 carbon atoms (=fluorinated $C_1$-$C_4$ alkylcarbonylamino), wherein one of the hydrogen atoms is replaced by a carbonylamino group (CO—NH—) and wherein at least one of the remaining hydrogen atoms, e.g. 1, 2, 3, or 4 of the hydrogen atoms are replaced by a fluorine atom, such as in trifluoroacetylamino and 3,3,3-trifluoropropionylamino.

$C_1$-$C_6$ Alkylthio (also termed as $C_1$-$C_6$-alkylsulfanyl) (or $C_1$-$C_6$-alkylsulfinyl or $C_1$-$C_6$-alkylsulfonyl, respectively) refer to straight-chain or branched alkyl groups having 1 to 6 carbon atoms, e.g. 1 to 4 carbon atoms, which are bound to the remainder of the molecule via a sulfur atom (or S(O)O in case of alkylsulfinyl or $S(O)_2O$ in case of alkylsulfonyl, respectively), at any bond in the alkyl group. Examples for $C_1$-$C_4$-alkylthio include methylthio, ethylthio, propylthio, isopropylthio, and n-butylthio. Examples for $C_1$-$C_4$-alkylsulfinyl include methylsulfinyl, ethylsulfinyl, propylsulfinyl, isopropylsulfinyl, and n-butylsulfinyl. Examples for $C_1$-$C_4$-alkylsulfonyl include methylsulfonyl, ethylsulfonyl, propylsulfonyl, isopropylsulfonyl, and n-butylsulfonyl.

Fluorinated $C_1$-$C_6$ alkylthio (also termed fluorinated $C_1$-$C_6$-alkylsulfanyl) is a straight-chain or branched alkylthio group having from 1 to 6, in particular 1 to 4 carbon atoms, wherein at least one, e.g. 1, 2, 3, 4 or all of the hydrogen atoms are replaced by fluorine atoms. Fluorinated $C_1$-$C_6$ alkylsulfinyl is a straight-chain or branched alkylsulfinyl group having from 1 to 6, in particular 1 to 4 carbon atoms, wherein at least one, e.g. 1, 2, 3, 4 or all of the hydrogen atoms are replaced by fluorine atoms. Fluorinated $C_1$-$C_6$ alkylsulfonyl is a straight-chain or branched alkylsulfonyl group having from 1 to 6, in particular 1 to 4 carbon atoms, wherein at least one, e.g. 1, 2, 3, 4 or all of the hydrogen atoms are replaced by fluorine atoms.

$C_3$-$C_6$ Cycloalkyl is a cycloaliphatic radical having from 3 to 6 C atoms, such as cyclopropyl, cyclobutyl, cyclopentyl and cyclohexyl. The cycloalkyl radical may be unsubstituted or may carry 1, 2, 3 or 4 $C_1$-$C_4$ alkyl radicals, preferably a methyl radical. One alkyl radical is preferably located in the 1-position of the cycloalkyl radical, such as in 1-methylcyclopropyl or 1-methylcyclobutyl. Likewise, $C_3$-$C_4$ Cycloalkyl is a cycloaliphatic radical having from 3 to 4 C atoms, such as cyclopropyl, cyclobutyl and 1-methylcyclopropyl.

Fluorinated $C_3$-$C_6$ cycloalkyl is a cycloaliphatic radical having from 3 to 6 C atoms, such as cyclopropyl, cyclobutyl, cyclopentyl and cyclohexyl, wherein at least one, e.g. 1, 2, 3, 4 or all of the hydrogen atoms are replaced by a fluorine atoms such as in 1-fluorocyclopropyl, 2-fluorocyclopropyl, (S)- and (R)-2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, or 1,2,2-trifluorocyclobutyl.

$C_2$-$C_6$-Alkenyl is a singly unsaturated hydrocarbon radical having 2, 3, 4, 5 or 6 C-atoms, e.g. vinyl, allyl (2-propen-1-yl), 1-propen-1-yl, 2-propen-2-yl, methallyl (2-methylprop-2-en-1-yl) and the like. $C_3$-$C_6$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

Fluorinated $C_2$-$C_6$-alkenyl is a singly unsaturated hydrocarbon radical having 2, 3, 4, 5 or 6 C-atoms, I, wherein at least one, e.g. 1, 2, 3, 4 or all of the hydrogen atoms are replaced by a fluorine atoms such as in 1-fluorovinyl, 2-fluorovinyl, 2,2-fluorovinyl, 3,3,3-fluoropropenyl, 1,1-difluoro-2-propenyl 1-fluoro-2-propenyl and the like.

$C_2$-$C_6$-Alkynyl is a hydrocarbon radical having a C—C-triple bond and 2, 3, 4, 5 or 6 C-atoms, e.g. ethynyl, propargyl, (2-propyn-1-yl), 1-propyn-1-yl, 2-butyn-1-yl 1-methyl-2-butyn-1-yl, 2-pentyn-1-yl, 2-hexyn-1-yl and the like.

$C_1$-$C_6$-Alkylene is a hydrocarbon bridging group having 1, 2, 3, 4, 5 or 6 carbon atoms, like methylene, ethylene, 1,2- and 1,3-propylene, 1,4-butylene and the like.

Examples of 5- or 6-membered heteroaromatic radicals include 2-, 3-, or 4-pyridyl, 2-, 4- or 5-pyrimidinyl, pyrazinyl, 3- or 4-pyridazinyl, 2- or 3-thienyl, 2- or 3-furyl, 2- or 3-pyrrolyl, 2-, 3- or 5-oxazolyl, 3-, 4- or 5-isoxazolyl, 2-, 3- or 5-thiazolyl, 3-, 4- or 5-isothiazolyl, 3-, 4- or 5-pyrazolyl, 2-, 4- or 5-imidazolyl, 2- or 5-[1,3,4]oxadiazolyl, 4- or 5-[1,2,3] oxadiazolyl, 3- or 5-[1,2,4]oxadiazolyl, 2- or 5-[1,3,4]thiadiazolyl, 2- or 5-[1,3,4]thiadiazolyl, 4- or 5-[1,2,3]thiadiazolyl, 3- or 5-[1,2,4]thiadiazolyl 1H-, 2H- or 3H-1,2,3-triazol-4-yl, 2H-triazol-3-yl, 1H-, 2H-, or 4H-1,2,4-triazolyl and 1H- or 2H-tetrazolyl.

Examples of fused saturated or unsaturated 5-, 6- or 7-membered carbocyclic rings include cyclopentano, 1,2-cyclopenteno, 2,3-cyclopenteno, 3,4 cyclopenteno, cyclohexano, 1,2-cyclohexeno, 2,3-cyclohexeno, 3,4-cyclohexeno, 1,2-cyclohexa-1,3-dieno, 2,3-cyclohexa-1,3-dieno, 3,4-cyclohexa-1,3-dieno, 4,5-cyclohexa-1,3-dieno, 5,6-cyclohexa-1,3-dieno, 1,2-cyclohexa-1,4-dieno, 1,2-cyclohexa-1,4-dieno, cycloheptano, 1,2-cyclohepteno, 2,3-cyclohepteno, 3,4-cyclohepteno, 1,2-cyclo-1,3-heptadieno and benzeno (benzo).

Examples for fused saturated or unsaturated 5-, 6- or 7-membered heterocyclic rings (as radicals $R^a$) comprise saturated or unsaturated, aromatic or non-aromatic heterocyclic rings. Examples therefore include fused 5- or 6-membered heteroaromatic radicals, such as thieno, furano, pyrrolo, pyrazolo, imidazolo, 1,2,3-triazolo, oxazolo, thiazolo, isoxazolo, isothiazolo, pyridino, pyrimidino, pyridazino, and also 5-, 6- or 7-membered saturated or mono-unsaturated heterocyclic rings di- and tetrahydrofurano, pyrrolino, pyrrolidino, oxopyrrolidino, pyrazolino, pyrazolidino, imidazolino, imidazolidino, oxazolino, oxazolidino, 2-oxo-oxazolidino, isoxazolino, isoxazolidino, piperidino, piperazino, morpholino, thiomorpholino, oxano, 1,4-dioxano and the like.

If $R^a$ and $R^b$ (and likewise $R^e$ and $R^f$) form together with N a 4-, 5-, 6- or 7-membered ring, examples for this type of radical comprise, apart from the above defined, 5- or 6-membered heteroaromatic radicals containing at least one N atom as ring member, azetidin-1-yl, azetin-1-yl, pyrrolin-1-yl, pyrrolidin-1-yl, pyrazolin-1-yl, pyrazolidin-1-yl, imidazolin-1-yl, imidazolidin-1-yl, oxazolin-1-yl, oxazolidin-1-yl, piperidin-1-yl, piperazin-1-yl, morpholin-4-yl and the like.

A first embodiment of the invention relates to compounds of the formula I, wherein X is O, NH or N—$C_1$-$C_4$-alkyl and wherein $R^1$ and $R^2$ are independently selected from the group consisting of H, $NH_2$, NH—$C_1$-$C_4$-alkyl, OH, O—$C_1$-$C_4$-alkyl, halogen, $C_2$-$C_4$-alkyl, $C_3$-$C_4$-cycloalkyl, $C_3$-$C_4$-alkenyl, fluorinated $C_1$-$C_4$-alkyl, fluorinated $C_3$-$C_4$-cycloalkyl, fluorinated $C_3$-$C_4$-alkenyl, formyl, $C_1$-$C_3$-alkylcarbonyl, and an aromatic radical Ar, which is selected from the group consisting of phenyl and a 5- or 6-membered C-bound heteroaromatic radical, wherein Ar carries 1 radical $R^{4x}$ which is selected from the group consisting of $C_2$-$C_6$-alkyl, $C_3$-$C_6$-cycloalkyl, $C_2$-$C_6$-alkoxy, fluorinated $C_2$-$C_6$-alkyl, fluorinated $C_3$-$C_6$-cycloalkyl, fluorinated $C_2$-$C_6$-alkoxy, $NR^eR^f$, 1-aziridinyl, azetidin-1-yl, pyrrolidin-1-yl, piperidin-1-yl and homopiperidin-1-yl, an optionally substituted phenyl group and an aromatic 5- or 6-membered C-bound heteroaromatic radical comprising 1 nitrogen atom as ring member and 0, 1, 2 or 3 further heteroatoms independently selected from O, S and N, wherein optional substituents comprise 1, 2, 3 or 4 radicals selected from H, halogen, cyano, $C_1$-$C_4$-alkyl and fluorinated $C_1$-$C_4$-alkyl;

or, taken together, $R^1$ and $R^2$ form a fused, saturated or unsaturated 5-, 6- or 7-membered C-bound carbocyclic or heterocyclic ring which may carry 1, 2 or 3 substituents $R^{4x}$ as defined above; and $R^3$ has one of the meanings given for $R^1$.

Amongst the compounds of this embodiment, preference is given to those, wherein X is NH.

A second embodiment relates to compounds of the formula I, which are different from the compounds of the first embodiment, i.e. at least one of the radicals $R^1$, $R^2$, $R^3$ is different from the meanings given for $R^1$, $R^2$, $R^3$ in this first embodiment or X is different from O, NH or N—$C_1$-$C_4$-alkyl. For example, the second embodiment relates to compounds of the formula I as defined herein, wherein $R^1$ and $R^2$ form a fused, saturated or unsaturated 5-, 6- or 7-membered C-bound carbocyclic or heterocyclic ring which carry 1, 2 or 3 substituents $R^4$ which are different from the aforementioned radicals $R^{4x}$. The second embodiment also relates to compounds of the formula I as defined herein, wherein X is different from O, NH or N—$C_1$-$C_4$-alkyl.

A further preferred embodiment relates to compounds of the formula I-A' and to the physiologically tolerated acid addition salts thereof:

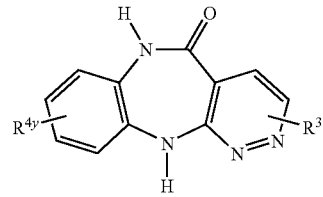

(I-A')

wherein $R^3$ and $R^{4y}$ are independently selected from the group consisting of H, $NH_2$, NH—$C_1$-$C_4$-alkyl, OH, O—$C_1$-$C_4$-alkyl, halogen, $C_2$-$C_4$-alkyl, $C_3$-$C_4$-cycloalkyl, $C_3$-$C_4$-alkenyl, fluorinated $C_1$-$C_4$-alkyl, fluorinated $C_3$-$C_4$-cycloalkyl, fluorinated $C_3$-$C_4$-alkenyl, formyl, $C_1$-$C_3$-alkylcarbonyl, and an aromatic radical Ar, which is selected from the group consisting of phenyl and a 5- or 6-membered C-bound heteroaromatic radical, wherein Ar carries 1 radical $R^y$ which is selected from the group consisting of $C_2$-$C_6$-alkyl, $C_3$-$C_6$-cycloalkyl, $C_2$-$C_6$-alkoxy, fluorinated $C_2$-$C_6$-alkyl, fluorinated $C_3$-$C_6$-cycloalkyl, fluorinated $C_2$-$C_6$-alkoxy, $NR^eR^f$, 1-aziridinyl, azetidin-1-yl, pyrrolidin-1-yl, piperidin-1-yl and homopiperidin-1-yl, an optionally substituted phenyl group and an aromatic 5- or 6-membered C-bound heteroaromatic radical comprising 1 nitrogen atom as ring member and 0, 1, 2 or 3 further heteroatoms independently selected from O, S and N, wherein optional substituents comprise 1, 2, 3 or 4 radicals selected from H, halogen, cyano, $C_1$-$C_4$-alkyl and fluorinated $C_1$-$C_4$-alkyl;

With regard to their use in a method of treatment according to the invention, compounds of the formula I are preferred, wherein X is a moiety N—$R^5$, wherein $R^5$ is as defined herein. In particular, $R^5$ is selected from H, C(O)—$R^c$, C(O)—$OR^d$ and C(O)—$NR^eR^f$, wherein $R^c$, $R^d$, $R^e$ and $R^f$ are as defined herein. In particular $R^c$ is hydrogen, $C_1$-$C_4$-alkyl or fluorinated $C_1$-$C_4$-alkyl; $R^d$ is in particular $C_1$-$C_4$-alkyl, $R^e$ and $R^f$ are preferably selected from hydrogen and $C_1$-$C_4$-alkyl or $NR^eR^f$ are together pyrrolidin-1-yl, piperidin-1-yl, piperazin-1-yl or morpholin-1-yl. Particular preference is given to compounds, wherein $R^5$ is H, i.e. X is NH.

Preference is also given to compounds of the formula I, wherein X is O.

With regard to their use in a method of treatment according to the invention, compounds of the formula I are preferred, wherein $R^1$ and $R^2$ together with the carbon atoms, to which they are attached, form a fused, saturated or unsaturated 5- or 6-membered C-bound carbocyclic or heterocyclic ring comprising 1 heteroatom, selected from nitrogen, oxygen and sulfur as ring member and 0, 1 or 2 further heteroatoms, independently selected from O, S and N, as ring members, wherein the fused ring is unsubstituted or may carry 1, 2 or 3 substituents, in particular 1 or 2 substituents, selected, independently of each other, from the group of radicals $R^4$ as defined herein.

Amongst these compounds particular preference is given to those compounds of the formula I, wherein $R^1$ and $R^2$ together with the carbon atoms, to which they are attached, form a fused benzene ring which is unsubstituted or may carry 1 or 2 substituents selected, independently of each other, from the group of radicals $R^4$ as defined herein. More preference is given to compounds of the formula I-A and the physiologically tolerated acid addition salts thereof (I-A)

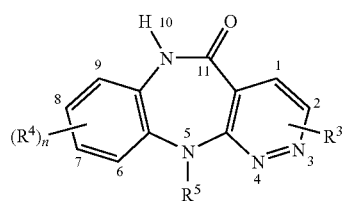

wherein n is 0, 1 or 2, in particular 0 or 1, and wherein $R^3$, $R^4$ and $R^5$ are as defined herein and in particular have independently of each other one of the meanings. More preference is given to the compounds of the formula I, wherein $R^5$ is hydrogen. The numbers in formula denominate the positions of the tricyclic core. The numbering is based on a nomenclature wherein the tricyclic core of I-A is regarded as a 3,4,5,10-tetraazadibenzo[a,d]cycloheptenone structure. The numbering scheme can be likewise applied to the compounds of the formulae I-B.1, I-B.2, I-B.3, I-B.4, I-E, I-F.1, I-F.2, I-F.3 and I-F.4.

Amongst the compounds, wherein $R^1$ and $R^2$ together with the carbon atoms, to which they are attached, form a fused heteroaromatic ring, particular preference is given to those compounds of the formula I, wherein $R^1$ and $R^2$ together with the carbon atoms, to which they are attached, form a fused pyridine ring, which is unsubstituted or carries 1 or 2 substituents selected, independently of each other, from the group of radicals $R^4$ as defined herein. More preference is given to compounds of the formulae I-B.1, I-B.2, I-B.3 and I-B.4 and to the physiologically tolerated acid addition salts thereof (I-B.1)

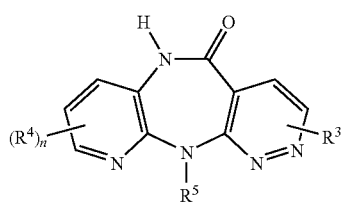

(I-B.2)

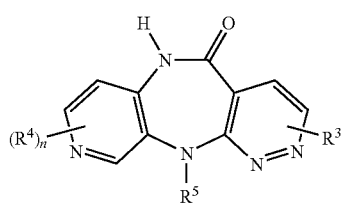

(I-B.3)

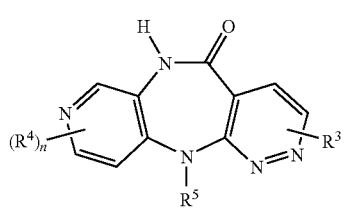

-continued (I-B.4)

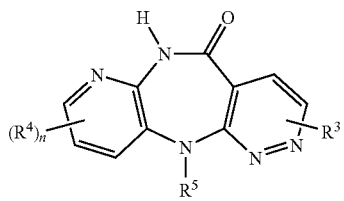

wherein n is 0, 1 or 2, in particular 0 or 1, and wherein $R^3$, $R^4$ and $R^5$ are as defined herein and in particular have independently of each other one of the meanings. More preference is given to the compounds of the formula I, wherein $R^5$ is hydrogen.

Particular preference is given to those compounds of the formula I, wherein $R^1$ and $R^2$ together with the carbon atoms, to which they are attached, form a fused thiophene ring, in particular a 2,3-b- or 4,5-b-fused thiophene ring, which is unsubstituted or carries 1 or 2 substituents selected, independently of each other, from the group of radicals $R^4$ as defined herein. More preference is given to compounds of the formulae I-C.1 and I-C.2 and to the physiologically tolerated acid addition salts thereof (I-C.1)

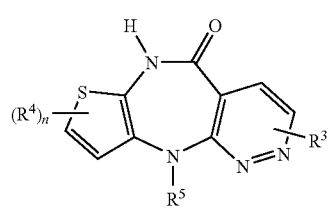

(I-C.2)

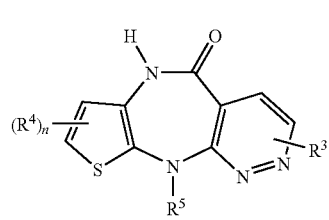

wherein n is 0, 1 or 2, in particular 0 or 1, and wherein $R^3$, $R^4$ and $R^5$ are as defined herein and in particular have independently of each other one of the preferred meanings. More preference is given to the compounds of the formula I, wherein $R^5$ is hydrogen.

Particular preference is also given to those compounds of the formula I, wherein $R^1$ and $R^2$ together with the carbon atoms, to which they are attached, form a fused thiazole ring which is unsubstituted or carries 1 substituent selected, independently of each other, from the group of radicals $R^4$ as defined herein. Amongst these, particular preference is given to the compounds of the formulae I-C.1 and I-D.2 and to the physiologically tolerated acid addition salts thereof

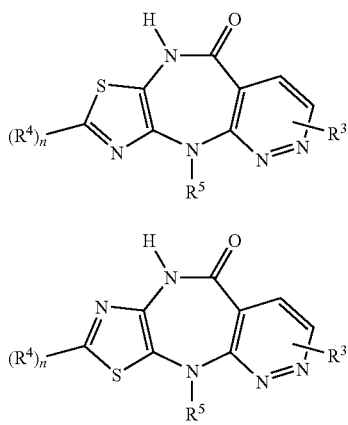

wherein n is 0 or 1, and wherein $R^3$, $R^4$ and $R^5$ are as defined herein and in particular have independently of each other one of the meanings. More preference is given to the compounds of the formula I, wherein $R^5$ is hydrogen.

Preference is also given to the compounds of the formulae I-E, I-F.1, I-F.2, I-F.3, I-F.4, I-G.1, I-G.2, I-H.1 and I-H.2 and to the physiologically tolerated acid addition salts thereof

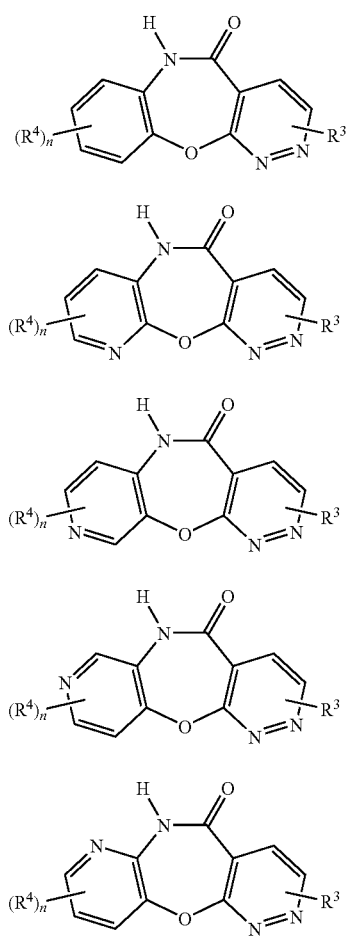

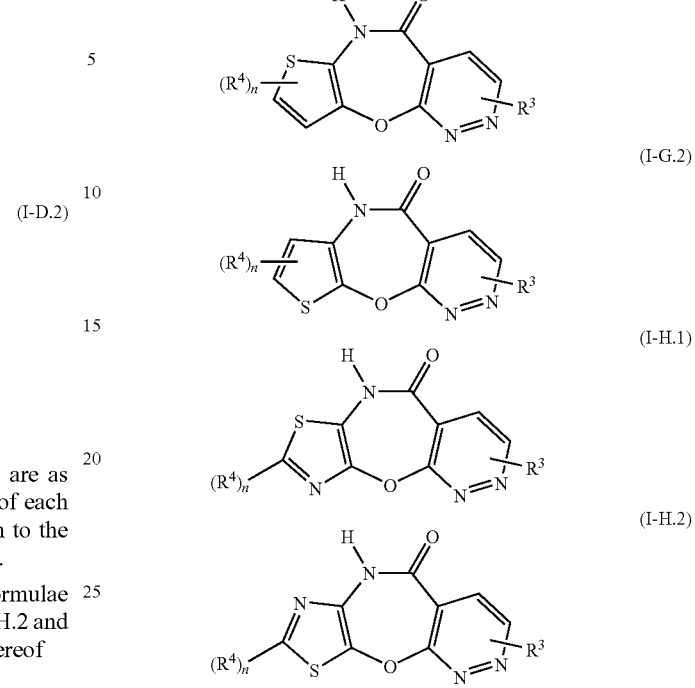

wherein n is 0, 1 or 2, in particular 0 or 1, and wherein $R^3$ and $R^4$ are as defined herein and in particular have independently of each other one of the preferred meanings.

Preference is given to compounds of the formula I (and likewise to compounds of the formulae I-A, I-B.1, I-B.2, I-B.3, I-B.4, IC.1, I-C.2, I-D.1, I-D.2, I-E, I-F.1, I-F.2, I-F.3, I-F.4, I-G.1, I-G.2, I-H.1 and I-H.2), wherein $R^3$ is selected from the group of hydrogen, halogen, OH, CN, nitro, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, $C_3$-$C_7$-cycloalkyl, $C_1$-$C_6$-alkoxy, fluorinated $C_1$-$C_6$-alkoxy, $C_1$-$C_6$-alkylthio, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, carboxy, $C_1$-$C_6$-alkyloxycarbonyl, fluorinated $C_1$-$C_6$-alkoxycarbonyl, $NR^aR^b$, $C(O)$—$NR^eR^f$, NH—C(O)—$NR^eR^f$, $NR^aR^b$—$C_1$-$C_6$-alkylene, O—$NR^aR^b$, phenyl and a 5- or 6-membered C- or N-bound heteroaromatic radical comprising 1 nitrogen atom as ring member and 0, 1, 2 or 3 further heteroatoms independently selected from O, S and N, as ring members, wherein phenyl and the heteroaromatic radical are, independently of each other, unsubstituted or carry 1, 2 or 3 substituents selected, independently of each other, from the group of radicals $R^{3b}$. In preferred embodiments, If $R^3$ is different from hydrogen, $R^3$ is preferably located at the carbon atom which is adjacent to the nitrogen atom of the pyridazine ring.

$R^3$ is particularly preferably hydrogen, halogen, CN, $NO_2$, OH, $C_1$-$C_4$-alkyl, fluorinated $C_1$-$C_4$-alkyl, $C_2$-$C_4$-alkenyl, $C_1$-$C_4$-alkoxy, fluorinated $C_1$-$C_4$-alkoxy, $C_1$-$C_4$-alkylthio, $C_1$-$C_4$-alkylcarbonyl, $NH_2$, $NH(C_1$-$C_4$-alkyl), $N(C_1$-$C_4$-alkyl)$_2$, $C(O)NH_2$, $C(O)NH(C_1$-$C_4$-alkyl), $C(O)N(C_1$-$C_4$-alkyl)$_2$, $C_3$-$C_7$-cycloalkyl, azetidin-1-yl, pyrrolidin-1-yl, piperidin-1-yl, piperazin-1-yl, morpholin-1-yl, homopiperidin-1-yl or a (hetero)aromatic radical which is selected from phenyl, 2-, 3 or 4-pyridyl, oxazol-2-yl, thiazol-2-yl or 2- or 3-thienyl, wherein the heteroaromatic radical is unsubstituted or substituted by 1 or 2 radicals selected from halogen, $C_1$-$C_4$-alkyl, $C_1$-$C_4$-alkoxy, fluorinated $C_1$-$C_4$-alkyl and fluorinated $C_1$-$C_4$-alkoxy.

Amongst the compounds, wherein $R^1$ and $R^2$ together with the carbon atoms, to which they are attached, form a fused ring, preference is given to those, wherein the fused ring is unsubstituted (i.e. wherein $R^4$ is absent) or which carries 1, 2 or 3, in particular 1 or 2 and more preferably 1 radical $R^4$ which is selected from the group of halogen, OH, CN, nitro, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, $C_3$-$C_7$-cycloalkyl, $C_1$-$C_6$-alkoxy, fluorinated $C_1$-$C_6$-alkoxy, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, carboxy, $C_1$-$C_6$-alkyloxycarbonyl, fluorinated $C_1$-$C_6$-alkoxycarbonyl, $NR^aR^b$, C(O)—$NR^eR^f$, NH—C(O)—$NR^e$ $R^f$, $NR^aR^b$-$C_1$-$C_6$-alkylene, O—$NR^aR^b$, phenyl and a 5- or 6-membered C- or N-bound heteroaromatic radical comprising 1 nitrogen atom as ring member and 0, 1, 2 or 3 further heteroatoms independently selected from O, S and N, as ring members, wherein phenyl and the heteroaromatic radical are, independently of each other, unsubstituted or carry 1, 2 or 3 substituents selected, independently of each other, from the group of radicals $R^{4b}$ as defined herein.

In particular $R^4$ is hydrogen or selected from halogen, nitro, cyano, $C_1$-$C_4$-alkoxy, fluorinated $C_1$-$C_4$-alkoxy, $NH_2$, $NH(C_1$-$C_4$-alkyl), $N(C_1$-$C_4$-alkyl)$_2$, $CH_2NH_2$, $CH_2NH(C_1$-$C_4$-alkyl), $CH_2N(C_1$-$C_4$-alkyl)$_2$, $C(O)NH_2$, $C(O)NH(C_1$-$C_4$-alkyl), $C(O)N(C_1$-$C_4$-alkyl)$_2$, a 4-, 5-, 6- or 7-membered saturated N-bound heterocyclic ring, which apart from the nitrogen atom may carry 1 further heteroatom, selected from O, S and N as a ring member, such as azetidin-1-yl, pyrrolidin-1-yl, piperidin-1-yl, piperazin-1-yl, morpholin-1-yl or homopiperidin-1-yl, which azetidin-1-yl, pyrrolidin-1-yl, piperidin-1-yl, piperazin-1-yl, morpholin-1-yl and homopiperidin-1-yl.

A particular preferred embodiment of the invention relates to compounds of the formula I-A, wherein n is 1 and $R^4$ is located in the 7-position. In this embodiment $R^4$ is preferably selected from halogen, nitro, cyano, $C_1$-$C_4$-alkoxy, fluorinated $C_1$-$C_4$-alkoxy, $NH_2$, $NH(C_1$-$C_4$-alkyl), $N(C_1$-$C_4$-alkyl)$_2$, $CH_2NH_2$, $CH_2NH(C_1$-$C_4$-alkyl), $CH_2N(C_1$-$C_4$-alkyl)$_2$, $C(O)NH_2$, $C(O)NH(C_1$-$C_4$-alkyl), $C(O)N(C_1$-$C_4$-alkyl)$_2$, a 4-, 5-, 6- or 7-membered saturated N-bound heterocyclic ring, which apart from the nitrogen atom may carry 1 further heteroatom, selected from O, S and N as a ring member, such as azetidin-1-yl, pyrrolidin-1-yl, piperidin-1-yl, piperazin-1-yl, morpholin-1-yl or homopiperidin-1-yl; which azetidin-1-yl, pyrrolidin-1-yl, piperidin-1-yl, piperazin-1-yl, morpholin-1-yl and homopiperidin-1-yl.

If present, the variables $R^a$, $R^b$, $R^c$, $R^d$, $R^e$ and $R^f$ independently have the following meanings:

$R^a$ and $R^b$ are preferably selected from hydrogen and $C_1$-$C_4$-alkyl or $NR^aR^b$ is a 4-, 5-, 6- or 7-membered saturated N-heterocyclic ring, which may carry 1 further heteroatom, selected from O, S and N as a ring member, such as azetidin-1-yl, pyrrolidin-1-yl, piperidin-1-yl, piperazin-1-yl, morpholin-1-yl or homopiperidin-1-yl;

$R^c$ is hydrogen, $C_1$-$C_4$-alkyl or fluorinated $C_1$-$C_4$-alkyl;

$R^d$ is $C_1$-$C_4$-alkyl, $R^e$ and $R^f$ are preferably selected from hydrogen and $C_1$-$C_4$-alkyl or $NR^eR^f$ is a 4-, 5-, 6- or 7-membered saturated N-heterocyclic ring, which may carry 1 further heteroatom, selected from O, S and N as a ring member, such as azetidin-1-yl, pyrrolidin-1-yl, piperidin-1-yl, piperazin-1-yl, morpholin-1-yl or homopiperidin-1-yl.

If present, the variables $R^{3a}$, $R^{3b}$, $R^{4a}$, $R^d$, $R^{4b}$ independently have the following meanings: halogen, $C_1$-$C_4$-alkyl, $C_1$-$C_4$-alkoxy, fluorinated $C_1$-$C_4$-alkyl or fluorinated $C_1$-$C_4$-alkoxy.

Particularly preferred compounds of the formula I are the compounds of the formula I-Aa and their acid addition salts.

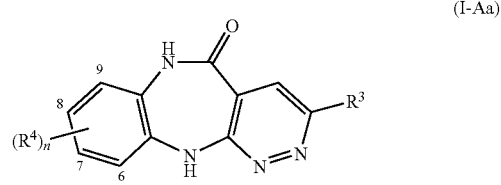

(I-Aa)

wherein n is 0, 1 or 2, in particular 0 or 1, and wherein $R^3$ and $R^4$ are as defined herein and in particular have independently of each other one of the preferred meanings. Examples or the particularly preferred compounds I-Aa are those, wherein $R^3$ and $(R^4)_n$ are given in the rows of table 1.

TABLE 1

| # | $(R^4)n$ | $R^3$ |
|---|---|---|
| 1 | — (n = 0) | H |
| 2 | — (n = 0) | F |
| 3 | — (n = 0) | Cl |
| 4 | — (n = 0) | Br |
| 5 | — (n = 0) | I |
| 6 | — (n = 0) | methyl |
| 7 | — (n = 0) | ethyl |
| 8 | — (n = 0) | propyl |
| 9 | — (n = 0) | CN |
| 10 | — (n = 0) | $NO_2$ |
| 11 | — (n = 0) | $NH_2$ |
| 12 | — (n = 0) | $NHCH_3$ |
| 13 | — (n = 0) | $N(CH_3)_2$ |
| 14 | — (n = 0) | azetidin-1-yl |
| 15 | — (n = 0) | pyrrolidin-1-yl |
| 16 | — (n = 0) | piperidin-1-yl |
| 17 | — (n = 0) | piperazin-1-yl |
| 18 | — (n = 0) | morpholin-4-yl |
| 19 | — (n = 0) | homopiperidin-1-yl |
| 20 | — (n = 0) | $CF_3$ |
| 21 | — (n = 0) | $OCF_3$ |
| 22 | — (n = 0) | OH |
| 23 | — (n = 0) | O—$CH_3$ |
| 24 | — (n = 0) | S—$CH_3$ |
| 25 | — (n = 0) | $CONH_2$ |
| 26 | — (n = 0) | CO—$CH_3$ |
| 27 | — (n = 0) | cyclopropyl |
| 28 | — (n = 0) | cyclobutyl |
| 29 | — (n = 0) | cyclopentyl |
| 30 | — (n = 0) | cyclohexyl |
| 31 | — (n = 0) | phenyl |
| 32 | — (n = 0) | pyrid-2-yl |
| 33 | — (n = 0) | pyrid-3-yl |
| 34 | — (n = 0) | pyrid-4-yl |
| 35 | — (n = 0) | oxaz-2-olyl |
| 36 | — (n = 0) | thiophen-2-yl |
| 37 | 7-$NO_2$ | Cl |
| 38 | 8-$NO_2$ | Cl |
| 39 | 9-$NO_2$ | Cl |
| 40 | 6-$NO_2$ | Cl |
| 41 | 7-CN | Cl |
| 42 | 8-CN | Cl |
| 43 | 9-CN | Cl |
| 44 | 6-CN | Cl |
| 45 | 7-F | Cl |
| 46 | 8-F | Cl |
| 47 | 9-F | Cl |
| 48 | 6-F | Cl |
| 49 | 7-Cl | Cl |

TABLE 1-continued

| # | (R⁴)n | R³ |
|---|---|---|
| 50 | 8-Cl | Cl |
| 51 | 9-Cl | Cl |
| 52 | 6-Cl | Cl |
| 53 | 7-Br | Cl |
| 54 | 8-Br | Cl |
| 55 | 9-Br | Cl |
| 56 | 6-Br | Cl |
| 57 | 7-OCH₃ | Cl |
| 58 | 8-OCH₃ | Cl |
| 59 | 9-OCH₃ | Cl |
| 60 | 6-OCH₃ | Cl |
| 61 | 7-azetidin-1-yl | Cl |
| 62 | 7-pyrrolidin-1-yl | Cl |
| 63 | 7-piperidin-1-yl | Cl |
| 64 | 7-piperazin-1-yl | Cl |
| 65 | 7-morpholin-4-yl | Cl |
| 66 | 7-homopiperidin-1-yl | Cl |
| 67 | 6-CONH₂ | Cl |
| 68 | 7-CONH₂ | Cl |
| 69 | 8-CONH₂ | Cl |
| 70 | 9-CONH₂ | Cl |
| 71 | 7-CH₂—NH₂ | Cl |

Particularly preferred examples of compounds of the formula I include
2-Chloro-11-oxo-10,11-dihydro-5H-3,4,5,10-tetraaza-dibenzo[a,d]cycloheptene-6-carboxylic acid amide (=3-Chloro-10-carboxamidopyridazino[3,4-b][1,5]benzodiazipin-5-one),
2-Chloro-5,10-dihydro-3,4,5,10-tetraaza-dibenzo[a,d]cyclohepten-11-one (=3-Chloropyridazino[3,4-b][1,5]benzodiazipin-5-one),
5,10-Dihydro-3,4,5,10-tetraaza-dibenzo[a,d]cyclohepten-11-one (=Pyridazino[3,4-b][1,5]benzodiazipin-5-one),
2-Chloro-8-nitro-5,10-dihydro-3,4,5,10-tetraaza-dibenzo[a,d]cyclohepten-11-one (=3-Chloro-8-nitropyridazino[3,4-b][1,5]benzodiazipin-5-one),
2-Chloro-5,10-dihydro-3,4,5,6,10-pentaaza-dibenzo[a,d]cyclohepten-11-one (=3-Chloro-8-nitropyridazino[3,4-b]-pyrido[2,3-f]-diazipin-5-one),
8-Chloro-5,10-dihydro-1,5,6,7,11-pentaaza-dibenzo[a,d]cyclohepten-10-one (=2-2-Chloro-5,10-dihydro-3,4,5,9,10-pentaaza-dibenzo[a,d]cyclohepten-11-one)
2-Bromo-5,10-dihydro-3,4,5,10-tetraaza-dibenzo[a,d]cyclohepten-11-one,
2-Iodo-5,10-dihydro-3,4,5,10-tetraaza-dibenzo[a,d]cyclohepten-11-one,
2-Vinyl-5,10-dihydro-3,4,5,10-tetraaza-dibenzo[a,d]cyclohepten-11-one,
2-Ethyl-5,10-dihydro-3,4,5,10-tetraaza-dibenzo[a,d]cyclohepten-11-one,
2-Chloro-7-(azetidin-1-yl)-5,10-dihydro-3,4,5,10-tetraaza-dibenzo[a,d]-cyclohepten-11-one,
2-Chloro-7-(pyrrolidin-1-yl)-5,10-dihydro-3,4,5,10-tetraaza-dibenzo[a,d]-cyclohepten-11-one,
2-Chloro-7-(piperidin-1-yl)-5,10-dihydro-3,4,5,10-tetraaza-dibenzo[a,d]-cyclohepten-11-one,
2-Chloro-7-(piperazin-1-yl)-5,10-dihydro-3,4,5,10-tetraaza-dibenzo[a,d]-cyclohepten-11-one,
2-Chloro-7-(morpholin-4-yl)-5,10-dihydro-3,4,5,10-tetraaza-dibenzo[a,d]-cyclohepten-11-one,
2-Chloro-7-(homopiperidin-1-yl)-5,10-dihydro-3,4,5,10-tetraaza-dibenzo[a,d]-cyclohepten-11-one,
and the physiologically tolerated acid addition salts thereof.

The compounds of the present invention can be prepared by analogy to routine techniques, a skilled person is familiar with. In particular, the compounds of the formula I can be prepared according to the following schemes:

Scheme 1:

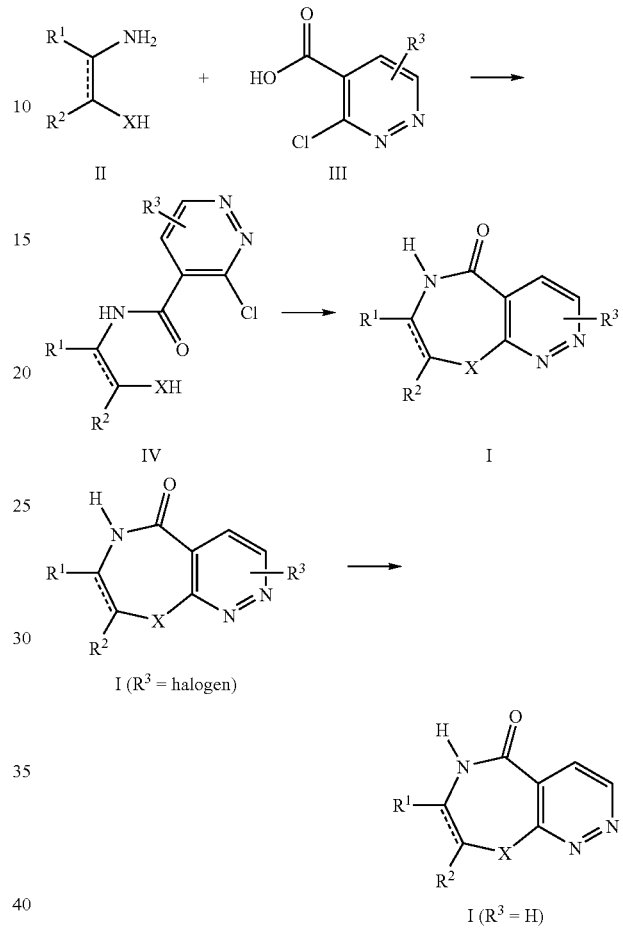

In scheme 1, $R^1$, $R^2$, and $R^3$ are as defined above, X is O, S or NH. ---- indicates a single bond or a double bond.

The amine II can be acylated by reaction with a 3-chloro-pyridazine-4-carboxylic acid III in the presence of a coupling agent such as carbonyl diimidazole. The reaction is preferably carried out in the presence of a basic solvent such as pyridine or N,N-dimethylformamide. The reaction is usually carried out at temperatures of from 40-120° C. The amide IV can be cyclized to give the polycyclic pyridazine compound I by heating in an acidic solvent such as acetic acid. In case that $R^3$ is halogen, the reduction of the halogen group can be carried out with a standard catalytic hydrogenation procedure such as the use of palladium-carbon under a hydrogen atmosphere to give the dehalogenated product 1. In case that $R^3$ is halogen, the halopyridazine compounds I can then be converted to the corresponding alkyl or aryl derivative I by Suzuki coupling methodology, to the corresponding alkenyl derivative by Stille or Heck methodology, to the corresponding amino derivative by Buchwald or Hartwig methodology according to standard methods of organic chemistry Tricyclic pyridazine compounds of the general formula I-A in which X is NH can be prepared according to a route depicted in scheme 2.

Scheme 2:

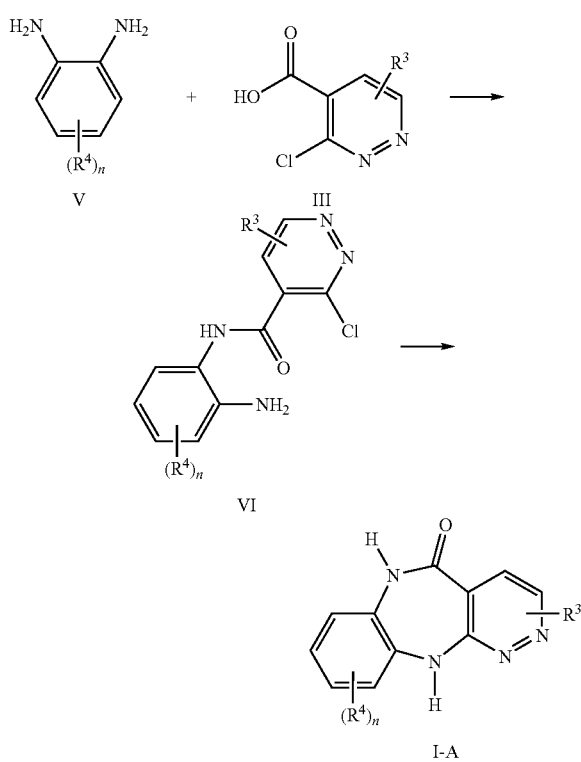

In scheme 2, n, $R^3$ and $R^4$ are as defined above.

A substituted 1,2-diaminobenzene compound V can be acylated by reaction with a 3-chloropyridazine-4-carboxylic acid III in the presence of a coupling agent such as carbonyl diimidazole. The reaction is preferably carried out in the presence of a basic solvent such as pyridine or N,N-dimethylformamide. The reaction is usually carried out at temperatures of from 40-120° C. The amide VI can be cyclized to give the tricyclic pyridazine compound I-A by heating in an acidic solvent such as acetic acid.

Tricyclic pyridazine compounds of the general formula I-A in which X is O or S can be prepared according to a route depicted in scheme 3.

Scheme 3:

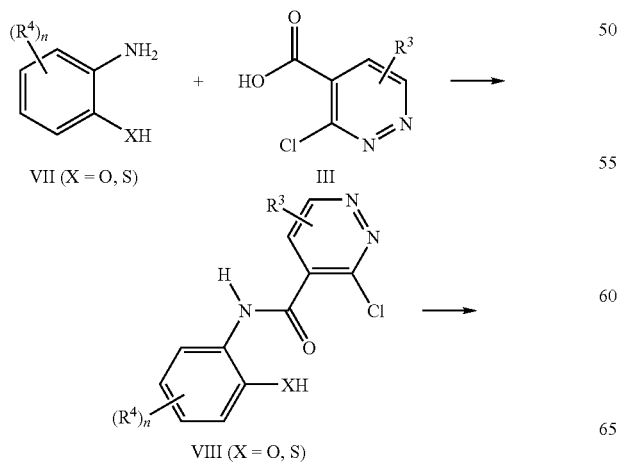

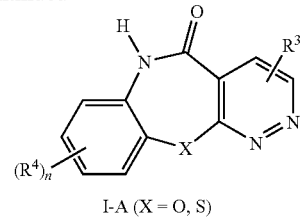

In scheme 3, n, $R^3$ and $R^4$ are as defined above.

The aniline VII can be selectively acylated on the amino position to give the amide VIII by reaction with a 3-chloro-pyridazine-4-carboxylic acid III according to a procedure described in scheme 2, above. The resultant amide VIII can be cyclized to give the tricyclic product I-A by heating to 40-120° C. in a suitable solvent such as dioxane in the presence of a base such as NaH. Related methodology is described by Ott et al (J. Med. Chem. 2004, 47, 4627).

Tricyclic pyridazine compounds of the general formula I-A in which X is $NR^5$ wherein $R^5$ has the meanings given above except of hydrogen can be prepared according to a route depicted in scheme 4.

Scheme 4:

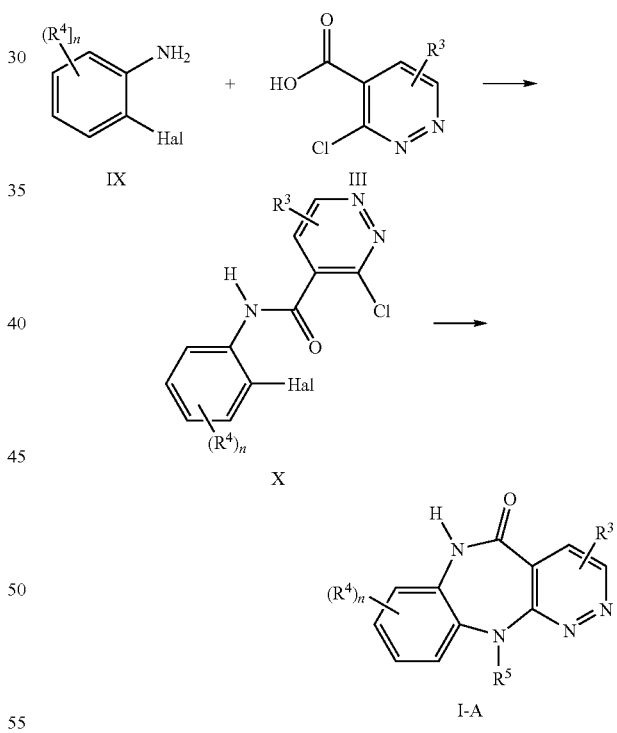

In scheme 4, n, $R^3$, $R^4$ are as defined above, Hal is halogen.

The haloaniline IX can be acylated on the amino position by reaction with a chloropyridazine-4-carboxylic acid III in the presence of a suitable coupling agent such as carbonyl diimidazole by heating to 40-120° C. in a basic solvent such as pyridine, or by reaction with triethylamine in a solvent such as dichloromethane. The resultant amide X can be cyclized to give the tricyclic amino product I-A by addition of an appropriate primary amine $NH_2R^5$ in a suitable solvent such as dioxane and then heating the product to 40-120° C. in a suitable solvent such as dioxane in the presence of a base such as NaH. Related methodology is described by Heinisch et al (Archiv der Pharmazie 1997, 330(1/2), 29-34).

Tricyclic pyridazine compounds of the general formula I-A, in which $R^3$ is alkyl, alkenyl, aryl or $NR^aR^b$ can be prepared according to a route depicted in scheme 5.

Scheme 5:

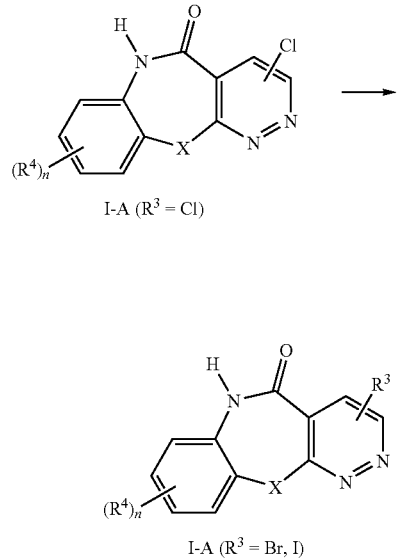

I-A ($R^3$ = Cl)

I-A ($R^3$ = Br, I)

In scheme 5, n, X and $R^4$ are as defined above.

A chloro-substituted pyridazine I-A can be converted to the corresponding bromo- or iodo-analog I-A by heating in the presence of hydrobromic acid or hydroiodic acid respectively. The resultant bromo- or iodo-derivative I-A can then be converted to the corresponding alkyl or aryl derivative I-A by Suzuki coupling methodology, to the corresponding alkenyl derivative by Stille or Heck methodology, to the corresponding amino derivative by Buchwald or Hartwig methodology according to standard methods of organic chemistry well known in the art and described e.g. in A. Suzuki, N. Miyaura, Chemical Reviews, 1995, 95, 2457-2483, C.-W. Huang, M. Shanmugasundaram, H.-M. Chang, C.-H. Cheng, Tetrahedron, 2003, 59, 3635-3641, S. P. H. Mee, V. Lee, J. E. Baldwin, Angew. Chem., 2004, 116, 1152-1156, N. Marion, E. C. Ecarnot, O. Navarro, D. Amoroso, A. Bell, S. P. Nolan, J. Org. Chem., 2006, 71, 3816-3821.

Tricyclic pyridazine compounds of the general formula I-A, in which $R^3$ is alkyl can also be prepared according to a route depicted in scheme 6.

Scheme 6:

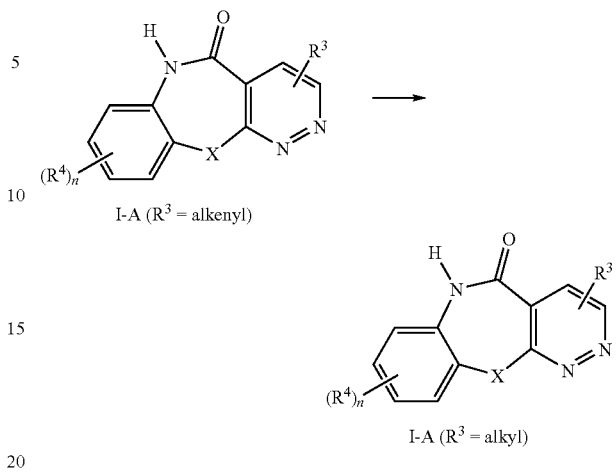

I-A ($R^3$ = alkenyl)

I-A ($R^3$ = alkyl)

In scheme 6, n, X and $R^4$ are as defined above.

The alkenyl derivative I-A obtainable according to a method as described in scheme 5 can be converted to the corresponding saturated alkyl derivative by reduction with a suitable catalyst such as Pd—C under an atmosphere of hydrogen in a suitable solvent such as methanol.

Tricyclic pyridazine compounds of the general formula I-A, in which $R^3$ is hydrogen, can be prepared according to a route depicted in scheme 7.

Scheme 7:

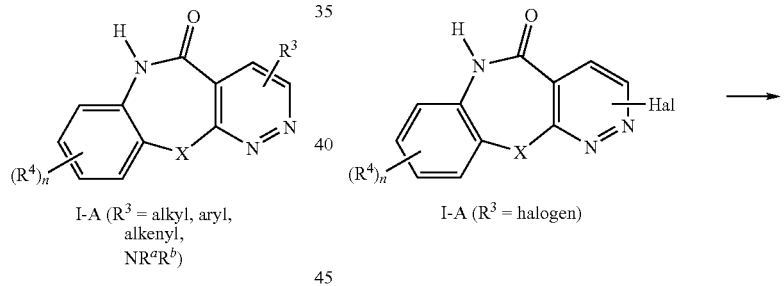

I-A ($R^3$ = alkyl, aryl, alkenyl, $NR^aR^b$)

I-A ($R^3$ = halogen)

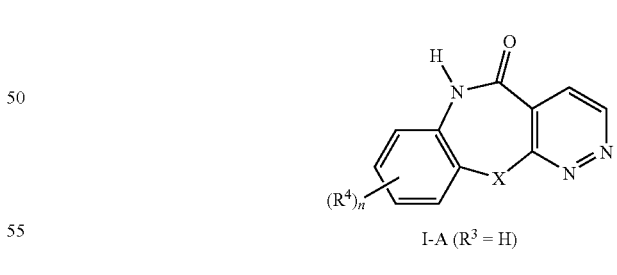

I-A ($R^3$ = H)

In scheme 7, n, X and $R^4$ are as defined above. $R^3$ is halogen

Compounds of the general formula I-A in which $R^3$ is halogen can be converted to compounds I-A in which $R^3$ is hydrogen by reduction of the halogen group according to standard catalytic hydrogenation procedure such as the use of palladium-carbon under a hydrogen atmosphere to give the dehalogenated product I-A.

As an illustration, the synthesis used to prepare Examples 1, 2 and 3 are shown in Schemes 8 and 9.

Scheme 8:

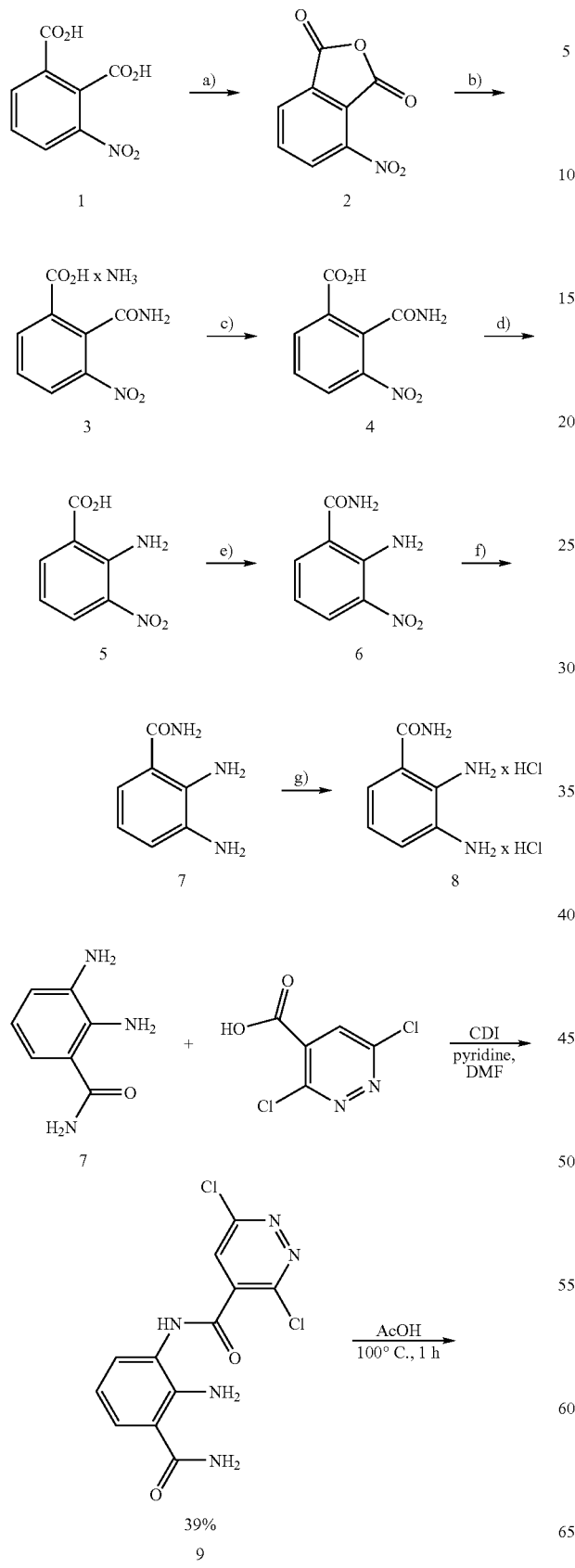

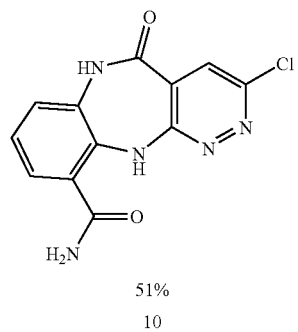

51%
10

The benzofuran-1,3-dione 2 can be prepared from the diacid 1 by heating in a solvent such as acetic anhydride. The amide 3 can be prepared by treatment of the benzofuran-1,3-dione 2 with a concentrated solution of ammonia in water. The free acid 4 is obtained by treatment with a suitable strong aqueous acid such as hydrochloric acid. Conversion of the amide compound 4 to an amino compound 5 can be accomplished by reaction with bromine and a strong aqueous base such as KOH, followed by reaction with a suitable strong aqueous acid such as hydrochloric acid. The carboxylic acid 5 can be converted to amide 6 by reaction with a suitable chlorinating agent such as thionyl chloride followed by treatment with a concentrated solution of ammonia in water. Reduction of the nitro group can be carried out with a standard catalytic hydrogenation procedure such as the use of palladium-carbon under a hydrogen atmosphere. The 1,2-diamine 7 can be stored by conversion to the more stable hydrochloride salt by reaction with hydrochloric acid. The 1,2-diamine 7 can be selectively acylated on the 1-amino position by reaction with 3,6-dichloropyridazine-4-carboxylic acid in the presence of a coupling agent such as carbonyl diimidazole by heating to 40-120° C. in a basic solvent such as pyridine. The amide 9 can be cyclized to give the tricyclic product 10 by heating in an acidic solvent such as acetic acid.

Scheme 9:

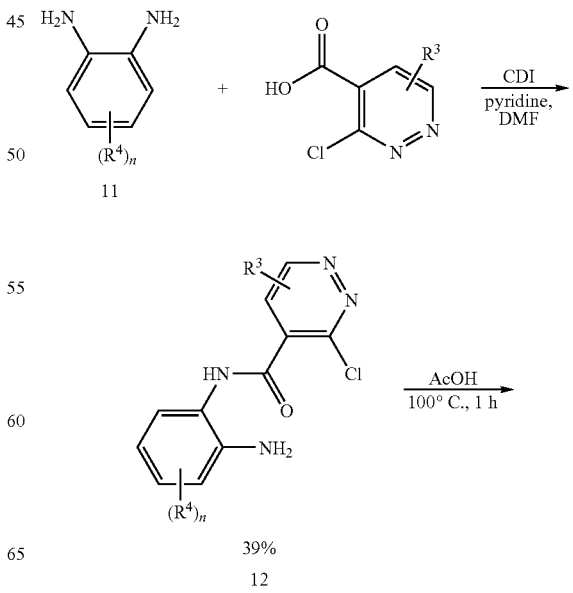

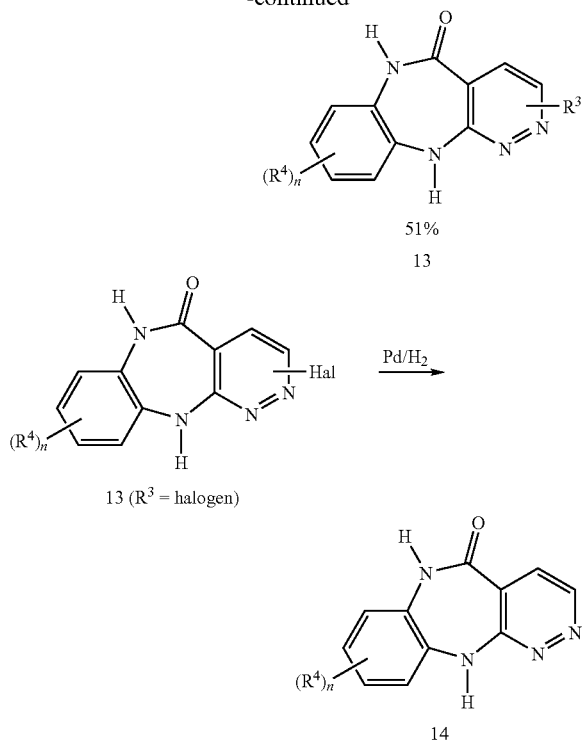

In the scheme 9, n, $R^3$ and $R^4$ have the meanings as given above.

A substituted 1,2-diamine 11 can be acylated by reaction with 3-chloropyridazine-4-carboxylic acid in the presence of a coupling agent such as carbonyl diimidazole (CDI) by heating to 40-120° C. in a basic solvent such as pyridine. The amide 12 can be cyclized to give the tricyclic product 13 by heating in an acidic solvent such as acetic acid. Reduction of the halogen group can be carried out with a standard catalytic hydrogenation procedure such as the use of palladium-carbon under a hydrogen atmosphere to give the dehalogenated product 14.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", Andrè Loupy (Ed.), Wiley-VCH 2002.

The acid addition salts of compounds I are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds of the formula I according to the present invention (and likewise the compounds of the formulae I-A, I-B.1, I-B.2, I-B.3, I-B.4, IC.1, I-C.2, I-D.1 and I-D.2) are capable of modulating the activity on glycogen synthase kinase 3β. In particular, the compounds of the formula I (and likewise the compounds of the formulae I-A, I-B.1, I-B.2, I-B.3, I-B.4, IC.1, I-C.2, I-D.1 and I-D.2) have an inhibitory activity on glycogen synthase kinase 3β. Amongst the compounds of the formula I those are preferred, which achieve effective inhibition at low concentrations. In particular, compounds of the formula I are preferred, which inhibit glycogen synthase kinase 3β at a level of $IC_{50}$<1 μMol, more preferably at a level of $IC_{50}$<0.5 μMol, particularly preferably at a level of $IC_{50}$<0.2 μMol and most preferably at a level of $IC_{50}$<0.1 μMol.

Therefore the compounds of the formula I according to the present invention and their physiologically tolerated acid addition salts are useful for the treatment of a medical disorder susceptible to treatment with a compound that modulates glycogen synthase kinase 3β activity. As mentioned above, diseases caused by abnormal GSK-3β activity and which thus can be treated by supplying the compound of the formula I and/or an acid addition salt thereof, include in particular neurodegenerative diseases such as Alzheimer's disease. In addition, the compounds of the present invention are also useful for treatment of other neurodegenerative diseases such as Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

Within the context of the treatment, the use according to the invention of the compounds of the formula I involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the ligands are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semi-solid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], 4$^{th}$ edition, Aulendorf: ECV-Editio-Kantor-Verlag, 1996.

The following examples serve to explain the invention without limiting it.

The compounds were either characterized via proton-NMR in $d_6$-dimethylsulfoxide or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts ($\delta$) expressed in parts per million (ppm). The relative area of the shifts in the $^1$H-NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

PREPARATION EXAMPLES

Example 1

2-Chloro-11-oxo-10,11-dihydro-5H-3,4,5,10-tetraaza-dibenzo[a,d]cycloheptene-6-carboxylic acid amide 4-Nitro-2-benzofuran-1,3-dione (2)

A solution of 474.8 g (2.25 mol) of 3-nitrophthalic acid in 450 ml of acetic anhydride was stirred under reflux for 1 h. The solution was slowly cooled to 80° C. Then 1000 ml of methyl-tert-butyl ether (MTBE) were added expeditiously and the solution was cooled to 15° C. The resulting solid was isolated, washed with MTBE and dried in a vacuum oven at 40° C. Yield: 88.8%

2-(Aminocarbonyl)-3-nitrobenzoic acid×NH$_3$ (3)

To 580 ml of ammonia (conc. aqueous solution) 400 g (2.07 mol) of 2 were added. The temperature rose to 60° C. and the mixture was stirred for 1 h. After addition of 200 ml of ethanol the mixture was cooled to 5° C. The resulting solid was isolated, washed with MTBE and dried in a vacuum oven at 40° C. Yield: 81.6%.

2-(Aminocarbonyl)-3-nitrobenzoic acid (4)

To a solution of 767 g (3.38 mol) of 3 in 1600 ml water at 38° C. 390 ml of 32% hydrochloric acid were added. The temperature rose to 55° C. 1000 ml of water were added to receive a less viscous liquid. The mixture was cooled to 15° C., the resulting solid was isolated, washed with 2000 ml of water and dried in a vacuum oven at 60° C. over KOH. Yield: 97%.

2-Amino-3-nitrobenzoic acid (5)

To a solution of 228.6 g of KOH in 500 ml of water 1500 g of ice were added. At −10° C. 72.7 g of bromine were added slowly. After complete addition the mixture was stirred for 10 minutes and 94.6 g (0.45 ml) of 4 were added. The mixture was stirred for 15 minutes at −10° C. and 1 h at 65° C. At 50-55° C. 260 ml of 32% hydrochloric acid were added. The colour changed to yellow. After the mixture was cooled to 25° C. the solid was isolated, washed with 3000 ml of water and dried in a vacuum oven at 60° C. over KOH. Yield: 98.8%.

2-Amino-3-nitrobenzamide (6)

To a solution of 100 g (0.55 mol) of acid 5 in 600 ml of tetrahydrofuran (THF) and 1 ml of N,N-dimethylformamide (DMF) 131 g (1.1 mol) of thionyl chloride were added. The mixture was stirred under reflux for 4 h and at room temperature for 12 h. The mixture was concentrated to 300 ml and added to a mixture of 1500 g of ice and 1500 ml of ammonia. The mixture was stirred for 3 h at 5° C. The resulting crystals were isolated at 10° C., washed with water, 100 ml of isopropanol, and 100 ml of MTBE and dried in a vacuum oven at 50° C. Recrystallisation from toluene/MTBE (3/1). Yield: 68%.

2,3-Diaminobenzamide (7)

The mixture of 206 g (1.14 mol) of 6 and 20.6 g of 10% Pd on charcoal in 824 ml of THF and 824 ml of methanol was hydrogenated with a total of 6 equivalents of hydrogen (130 l) at 2048° C. over 24 h. The mixture was filtrated and the solvents were evaporated.

2,3-Diaminobenzamide×2 HCl (8)

A suspension of 7 in 721 ml of methanol and 51.5 g of charcoal was stirred for 1 h. After filtration 518.8 g of 20% HCl in isopropanol were added to the filtrate. During the exothermic reaction the temperature rose to 42° C. The mixture was cooled to 0-5° C. The resulting solid was isolated, washed with methanol and acetone and dried in a vacuum oven at 40° C. Yield: 89%.

3,6-Dichloro-pyridazine-4-carboxylic acid (2-amino-3-carbamoylphenyl)-amide (9)

3,6-Dichloropyridazine-4-carboxylic acid (1.15 g, 5.96 mmol) and 1,1'-carbonyldiimidazole (CDI (0.97 g) in DMF (25 ml) were stirred at room temperature for 2 h. A solution of 2,3-diaminobenzamide (1.30 g, 5.96 mmol) in pyridine (25 ml) was added and the solution heated at 50° C. for 4 h. The cooled solution was concentrated and partitioned between ethyl acetate (EtOAc) and water, the organic layer separated, dried, filtered and concentrated to give the product.
$^1$H-NMR (DMSO-$d_6$, 300 MHz) δ 6.53 (br s, 2H), 6.62 (t, 1H), 7.25 (br s, 1H), 7.39 (m, 1H), 7.55 (d, 1H), 7.90 (br s, 1H), 8.56 (s, 1H), 10.08 (s, 1H).

2-Chloro-11-oxo-10,11-dihydro-5H-3,4,5,10-tetraaza-dibenzo[a,d]cycloheptene-6-carboxylic acid amide (10)

3,6-Dichloro-pyridazine-4-carboxylic acid (2-amino-3-carbamoyl-phenyl)-amide (500 mg, 1.53 mmol) in acetic acid (AcOH) (25 ml) was heated at 100° C. for 1 h. The cooled solution was concentrated and partitioned between EtOAc and saturated Na—HCO$_3$, the organic layer separated, dried, filtered and concentrated to give the product as a brown solid (227 mg, 51%).
$^1$H-NMR (DMSO-$d_6$, 300 MHz) δ 7.45 (t, 1H), 7.75 (br s, 1H), 8.00 (dd, 2H), 8.56 (s, 1H), 8.82 (br s, 1H), 14.05 (br s, 1H); MS (APCI$^+$) m/z 290 (M+H$^+$, 100%).

Example 2

2-Chloro-5,10-dihydro-3,4,5,10-tetraaza-dibenzo[a,d]cyclohepten-11-one

Prepared by the method described for Example 1.
$^1$H-NMR (DMSO-$d_6$, 300 MHz) δ 7.52 (m, 2H), 7.90 (m, 2H), 8.77 (s, 1H), 14.20 (br s, 1H); MS (APCI+) m/z 247 (M+H$^+$, 100%).

Example 3

5,10-Dihydro-3,4,5,10-tetraaza-dibenzo[a,d]cyclohepten-11-one

The product from Example 2 (50 mg, 0.20 mmol) was dissolved in methanol (MeOH) (10 ml) and Pd—C (10%, 10 mg) was added. The reaction was stirred under hydrogen (1 atm) for 4 hours. The catalyst was removed by filtration and the solution concentrated to give a residue which was purified by chromatography (CH$_2$Cl$_2$:MeOH, 4:1) to give the product as a white solid (12 mg, 28%).
$^1$H-NMR (DMSO-$d_6$, 300 MHz) δ 7.22 (m, 2H), 7.71 (m, 2H), 8.13 (d, 1H), 8.32 (d, 1H), 12.41 (br s, 1H), 13.43 (br s, 1H); MS (APCI$^+$) m/z213 (M+H$^+$, 100%).

Example 4

2-Chloro-8-nitro-5,10-dihydro-3,4,5,10-tetraaza-dibenzo[a,d]cyclohepten-11-one

Prepared by the method described for Example 1. Yield: 31%.
$^1$H-NMR (DMSO-$d_6$, 300 MHz) δ 7.52 (m, 2H), 7.90 (m, 2H), 8.77 (s, 1H), 14.20 (br s, 1H); MS (APCI+) m/z292 (M+H$^+$, 100%).

Example 5

2-Chloro-5,10-dihydro-3,4,5,6,10-pentaaza-dibenzo[a,d]cyclohepten-11-one

Prepared by the method described for Example 1. Yield: 33%.
$^1$H-NMR (DMSO-$d_6$, 300 MHz) δ 7.52 (m, 2H), 7.90 (m, 2H), 8.77 (s, 1H), 14.20 (br s, 1H); MS (APCI$^+$) m/z 248 (M+H$^+$, 100%).

Example 6 (Comparative)

11-Oxo-10,11-dihydro-5H-dibenzo[b,e][1,4]diazepine-6-carboxylic acid amide

Prepared by the method described for Example 1. Yield: 62%.
MS (APCI$^+$) m/z254 (M+H$^+$, 100%).

Example 7

8-Chloro-5,10-dihydro-1,5,6,7,11-pentaaza-dibenzo[a,d]cyclohepten-11-one

Prepared by the method described for Example 1. Yield: 37%.
$^1$H-NMR (DMSO-$d_6$, 300 MHz) δ 6.95 (t, 1H), 7.87 (d, 1H), 7.96 (d, 1H), 8.81 (s, 1H), 10.91 (s, 1H), 14.18 (br s, 1H); MS (APCI+) m/z248 (M+H$^+$, 100%).

Example 8

2-Bromo-5,10-dihydro-3,4,5,10-tetraaza-dibenzo[a,d]cyclohepten-11-one

2-Chloro-5,10-dihydro-3,4,5,10-tetraaza-dibenzo[a,d]cyclohepten-11-one from Example 2 (400 mg, 1.62 mmol) was added to HBr (10 ml, 47% in water) and heated at 100° C. for 63 hours. The solution was cooled and diluted with EtOAc and NaOH (1M). The resultant precipitate was collected by filtration, washed with EtOAc and water and then dried under vacuum to give the title compound as a white solid (170 mg, 36%).
$^1$H-NMR (DMSO-$d_6$, 300 MHz) δ 7.27 (m, 2H), 7.54 (s, 1H), 7.68 (s, 1H), 8.21 (s, 1H), 13.70 (br s, 1H); MS (APCI+) m/z 291.0, 293.0 (M+H$^+$, 100%).

Example 9

2-Iodo-5,10-dihydro-3,4,5,10-tetraaza-dibenzo[a,d]cyclohepten-11-one

Prepared using HI (57% in water) by the method described for Example 8. Yield: 31%.

$^1$H-NMR (DMSO-d$_6$, 300 MHz) δ 7.08 (m, 2H), 7.52 (s, 1H), 7.68 (s, 1H), 8.01 (s, 1H), 13.50 (br s, 1H); MS (APCI+) m/z 339.0 (M+H$^+$, 100%).

Example 10

2-Vinyl-5,10-dihydro-3,4,5,10-tetraaza-dibenzo[a,d]cyclohepten-11-one

To a solution of 2-chloro-5,10-dihydro-3,4,5,10-tetraaza-dibenzo[a,d]cyclohepten-11-one from Example 2 (150 mg, 0.61 mmol) in toluene (3 ml) was added tri-n-butyl(vinyl)tin (231 mg, 0.73 mmol) followed by triphenylphosphine (4.8 mg, 0.02 mmol) and tetrakistriphenylphosphine palladium (7 mg, 0.01 mmol) and the resulting mixture was heated at 100° C. for 15 hours. The mixture was cooled to room temperature, concentrated in vacuo and purified directly by flash column chromatography (silica gel, 10% MeOH 90% dichloromethane) to afford the title compound as a yellow solid (47 mg, 33%).

$^1$H-NMR (DMSO-d$_6$, 300 MHz) isomers: δ 5.43 (m, 0.5H), 5.63 (m, 0.5H), 6.01 (m, 0.5H), 6.10 (m, 0.5H), 6.43 (m, 0.5H), 6.70 (m, 0.5H), 7.20 (m, 2H), 7.70 (m, 2H), 8.09 (s, 1H), 13.40 (br s, 1H); MS (APCI+) m/z 239.1 (M+H$^+$, 100%).

Example 11

2-Ethyl-5,10-dihydro-3,4,5,10-tetraaza-dibenzo[a,d]cyclohepten-11-one

A solution of 2-vinyl-5,10-dihydro-3,4,5,10-tetraaza-dibenzo[a,d]cyclohepten-11-one from Example 10 (40 mg, 0.17 mmol) and 5 mg of palladium on charcoal (10%) in 50 ml of methanol was stirred under 1 atm of hydrogen for 70 min. Filtration and evaporation to dryness afforded the title compound as a pale yellow solid (41 mg, 87%).

MS (APCI$^+$) m/z 241.1 (M+H$^+$, 100%).

The compounds according to the invention exhibit very good affinities for GSK-3 (<1 µM, frequently <100 nM) and exhibited good selectivity against multiple kinase targets.

Methods—Biochemical hGSK-3Beta Assay

Compounds were tested for their ability to inhibit human Glycogen Synthase Kinase-3 beta (hGSK-3β) to phosphorylate biotin-YRRAAVPPSPSLSRHSSPHQ(pS)EDEEE. Compounds were incubated with 0.5 µCi 33P-ATP, 10 µM ATP, 0.0125 U hGSK-3β (Upstate cell signaling solutions) and 1 µM substrate (biotin-YRRAAVPPSPSLSRHSSPHQ(pS)EDEEE) in 50 mM HEPES, 10 mM MgCl$_2$, 100 mM Na$_3$VO$_4$, 1 mM DTT, 0.0075% Triton, 2% DMSO (total volume 50 µL) for 30 minutes at room temperature. The incubation was stopped by addition of an equal volume of 100 mM EDTA, 4M NaCl. 80 µL of this mixture was added to streptavidin-coated Flashplates (PerkinElmer). Following a wash step, 33P incorporation was quantified on a MicroBeta microplate liquid scintillation counter (PerkinElmer). IC$_{50}$'s were determined by fitting a sigmoidal dose-response curve to the counts obtained at the different concentrations in GraphPad Prism.

Methods—β-Catenin Reporter-Gene Assay

Compounds were tested for their ability to modulate β-catenin-modulated gene transcription in a LEF/TCF (T-cell factor) reporter gene assay. SY-SY5Y human neuroblastoma cells were transiently transfected with 80 ng/well TOP-FLASH plasmid (Up-state cell signaling solutions) containing two sets of three copies of the TCF binding site upstream of the Thymidine Kinase minimal promoter and firefly Luciferase open reading frame or with 80 ng/well FOP-FLASH plasmid (Upstate cell signaling solutions) containing three copies of a mutated TCF binding site upstream of the Thymidine Kinase minimal promoter and firefly Luciferase open reading frame. In addition all cells were transiently transfected with the 20 ng/well pRL-TK plasmid (Promega) containing the herpes simplex virus thymidine kinase promoter to provide low to moderate levels of *Renilla* Luciferase expression. Transfection medium was exchanged for serum-free medium containing the test substance and incubated for 24 h at 37 degreed C. The incubation was stopped and quantified using the Dual Glo Luciferase Assay (Promega) as indicated and quantified on a Pherastar reader (BMG).

Firefly Luciferase activity was normalised for *Renilla* Luciferase activity per well. Subsequently, the normalised TOPFLASH response was compared to the normalised FOP-FLASH response, thus giving the LEF/TCF specific signal. The maximal response is the maximal ratio between the normalised TOPFLASH and FOPFLASH signals. Sigmoidal dose-response curves were fitted using Graphpad Prism.

The results of the binding tests are given in the table below.

| Example # | GSK-3β IC$_{50}$ (nM) | Cellular Activity in GSK-3β TOPFLASH assay |
|---|---|---|
| 1 | 70.0 | +++ |
| 2 | 95.5 | ++ |
| 3 | 302 | + |
| 4 | 625 | n.d. |
| 6 (comparative) | 57,000 | INACTIVE |
| 7 | 101 | ++ |
| 9 | 42 | n.d. |
| 10 | 45 | n.d. | n.d. not determined

We claim:
1. A compound of formula I

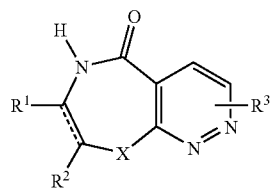

or a physiologically tolerated acid addition salt thereof, wherein

---- indicates a single bond or a double bond;

X is O, S or N—R$^5$;

R$^1$, R$^2$ are independently selected from the group consisting of H, NH$_2$, NH—C$_1$-C$_6$-alkyl, OH, =O, C$_1$-C$_6$-alkoxy, halogen, methyl, C$_2$-C$_4$-alkyl, C$_3$-C$_4$-cycloalkyl, C$_3$-C$_4$-alkenyl, fluorinated C$_1$-C$_4$-alkyl, fluorinated C$_3$-C$_4$-cycloalkyl, fluorinated C$_3$-C$_4$-alkenyl, formyl, C$_1$-C$_3$-alkylcarbonyl, and an aromatic radical Ar, which is selected from the group consisting of phenyl and a 5- or 6-membered C-bound heteroaromatic radical, comprising 1 nitrogen atom as ring member and 0, 1, 2 or 3 further heteroatoms, independently selected from 0, S and N, as ring members, wherein Ar is unsubstituted or carries 1 radical R$_{1a}$ or, R$^1$ and R$^2$ together with the carbon atoms, to which they are attached, form a fused, saturated or unsaturated 5-, 6- or 7-membered C-bound carbocyclic or heterocyclic ring comprising 1 heteroatom, selected from nitrogen, oxygen and sulfur as ring member and 0, 1 or 2 further heteroatoms, independently selected from O, S and N, as ring members, wherein the fused ring is unsubstituted or may carry 1, 2 or 3 substituents selected, independently of each other, from the group of radicals $R^4$ as defined below;

$R^3$ is selected from the group consisting of H, OH, halogen, CN, nitro, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, fluorinated $C_2$-$C_6$-alkenyl, $C_2$-$C_6$-alkynyl, $C_3$-$C_7$-cycloalkyl, fluorinated $C_3$-$C_7$-cycloalkyl, $C_1$-$C_6$-alkoxy, $C_1$-$C_6$-hydroxyalkoxy, $C_1$-$C_6$-alkoxy-$C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, carboxy, $C_1$-$C_6$-alkyloxycarbonyl, fluorinated $C_1$-$C_6$-alkoxycarbonyl, $NR^aR^b$, $C(O)$—$NR^eR^f$, NH—$C(O)$—$NR^eR^f$, $NR^aR^b$—$C_1$-$C_6$-alkylene, O—$NR^aR^b$, phenylsulfonyl, benzyloxy, phenoxy, where the phenyl radical in the 3 last-mentioned radicals may be unsubstituted or may carry 1, 2 or 3 substituents selected, independently of each other, from the group of radicals $R^{3a}$, phenyl and a 5- or 6-membered C- or N-bound heteroaromatic radical comprising 1 nitrogen atom as ring member and 0, 1, 2 or 3 further heteroatoms independently selected from O, S and N, as ring members, wherein phenyl and the heteroaromatic radical are, independently of each other, unsubstituted or carry 1, 2 or 3 substituents selected, independently of each other, from the group of radicals $R^{3b}$;

$R^4$ is selected from the group consisting of OH, halogen, CN, nitro, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, fluorinated $C_2$-$C_6$-alkenyl, $C_3$-$C_7$-cycloalkyl, fluorinated $C_3$-$C_6$-cycloalkyl, $C_1$-$C_6$-alkoxy, $C_1$-$C_6$-hydroxyalkoxy, $C_1$-$C_6$-alkoxy-$C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, carboxy, $C_1$-$C_6$-alkyloxycarbonyl, fluorinated $C_1$-$C_6$-alkoxycarbonyl, $NR^aR^b$, $C(O)$—$NR^eR^f$, NH—$C(O)$—$NR^eR^f$, $NR^aR^b$—$C_1$-$C_6$-alkylene, O—$NR^aR^b$, phenylsulfonyl, benzyloxy, phenoxy, where the phenyl radical in the 3 last-mentioned radicals may be unsubstituted or may carry 1, 2 or 3 substituents selected, independently of each other, from the group of radicals $R^{4a}$, phenyl and a 5- or 6-membered C- or N-bound heteroaromatic radical comprising 1 nitrogen atom as ring member and 0, 1, 2 or 3 further heteroatoms independently selected from O, S and N, as ring members, wherein phenyl and the heteroaromatic radical are, independently of each other, unsubstituted or carry 1, 2 or 3 substituents selected, independently of each other, from the group of radicals $R^{4b}$;

$R^5$ is selected from the group consisting of H, $C_1$-$C_6$-alkyl, $C_2$-$C_6$-alkenyl, $C(O)$—$R^c$, $C(O)$—$OR^d$, $C(O)$—$NR^eR^f$; and wherein $R^{1a}$ is selected from the group consisting of halogen, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $NR^eR^f$, 1-aziridinyl, azetidin-1-yl, pyrrolidin-1-yl, piperidin-1-yl, morpholin-4-yl and homopiperidin-1-yl, a phenyl group or an aromatic 5- or 6-membered C-bound heteroaromatic radical comprising 1 nitrogen atom as ring member and 0, 1, 2 or 3 further heteroatoms independently selected from O, S and N, as ring members, wherein phenyl and the heteroaromatic radical are, independently of each other, unsubstituted or substituted by 1, 2, 3 or 4 radicals selected from halogen, cyano, $C_1$-$C_4$-alkyl, fluorinated $C_1$-$C_4$-alkyl, $C_1$-$C_4$-alkoxy and fluorinated $C_1$-$C_4$-alkoxy;

$R^{3a}$, $R^{4a}$ are independently selected from the group consisting of halogen, CN, nitro, OH, $C_1$-$C_4$-alkyl, fluorinated $C_1$-$C_4$-alkyl, $C_1$-$C_4$-alkoxy and fluorinated $C_1$-$C_4$-alkoxy $C_1$-$C_4$-alkylcarbonyl, fluorinated $C_1$-$C_4$-alkylcarbonyl, $C_1$-$C_4$-alkylcarbonylamino, fluorinated $C_1$-$C_4$-alkylcarbonylamino, carboxy, $C_1$-$C_6$-alkyloxycarbonyl, fluorinated $C_1$-$C_6$-alkoxycarbonyl, $C(O)$—$NR^eR^f$, NH—$C(O)$—$NR^eR^f$, $NR^aR^b$, $NR^aR^b$—$C_1$-$C_6$-alkylene, O—$NR^aR^b$, $R^{3b}$, $R^{4b}$ are independently selected from the group consisting of halogen, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $NR^eR^f$, 1-aziridinyl, azetidin-1-yl, pyrrolidin-1-yl, piperidin-1-yl, piperazin-1-yl, morpholin-4-yl and homopiperidin-1-yl, a phenyl group or an aromatic 5- or 6-membered C-bound heteroaromatic radical comprising 1 nitrogen atom as ring member and 0, 1, 2 or 3 further heteroatoms independently selected from O, S and N, as ring members, wherein phenyl and the heteroaromatic radical are, independently of each other, unsubstituted or substituted by 1, 2, 3 or 4 radicals selected from halogen, cyano, $C_1$-$C_4$-alkyl, fluorinated $C_1$-$C_4$-alkyl, $C_1$-$C_4$-alkoxy and fluorinated $C_1$-$C_4$-alkoxy;

$R^a$, $R^b$ are independently selected from the group consisting of H, $C_1$-$C_4$-alkyl, fluorinated $C_1$-$C_4$-alkyl or $C_1$-$C_4$-alkoxy or may form, together with N, a 4-, 5-, 6- or 7-membered saturated or unsaturated N-heterocyclic ring, which may carry 1 further heteroatom, selected from O, S and N as a ring member;

$R^c$ is selected from the group consisting of hydrogen, $C_1$-$C_6$-alkyl, $C_3$-$C_6$-cycloalkyl, fluorinated $C_1$-$C_6$-alkyl, fluorinated $C_3$-$C_6$-cycloalkyl, phenyl wherein phenyl is unsubstituted or substituted by 1, 2, 3 or 4 radicals selected from halogen, cyano, $C_1$-$C_4$-alkyl, fluorinated $C_1$-$C_4$-alkyl, $C_1$-$C_4$-alkoxy and fluorinated $C_1$-$C_4$-alkoxy;

$R^d$ is $C_1$-$C_6$-alkyl, $C_3$-$C_6$-cycloalkyl, fluorinated $C_1$-$C_6$-alkyl, fluorinated $C_3$-$C_6$-cycloalkyl, phenyl wherein phenyl is unsubstituted or substituted by 1, 2, 3 or 4 radicals selected from halogen, cyano, $C_1$-$C_4$-alkyl, fluorinated $C_1$-$C_4$-alkyl, $C_1$-$C_4$-alkoxy and fluorinated $C_1$-$C_4$-alkoxy;

$R^e$ and $R^f$ are independently selected from the group consisting of H, $C_1$-$C_4$-alkyl, fluorinated $C_1$-$C_4$-alkyl or $C_1$-$C_4$-alkoxy or may form, together with N, a 4-, 5-, 6- or 7-membered saturated or unsaturated N-heterocyclic ring, which may carry 1 further heteroatom, selected from O, S and N as a ring member, except for pyridazino[3,4-b][1,5]benzoxazepin-5(6H)-one, 3-chloropyridazinobenzo[3,4-b][1,5]benzoxazepin-5(6H)-one, 3,8-dichloropyridazino[3,4-b][1,5]benzoxazepin-5(6H)-one, 3-chloro-8-trifluoromethylpyridazino[3,4-b][1,5]benzoxazepin-5(6H)-one, 3-chloro-9-trifluoromethylpyridazino[3,4-b][1,5]benzoxazepin-5(6H)-one, 3-chloro-8-methylpyridazino[3,4-b][1,5]benzoxazepin-5(6H)-one, 3-chloro-9-methylpyridazino[3,4-h][1,5]benzoxazepin-5(6H)-one, 3-chloro-8-methoxypyridazino[3,4-b][1,5]benzoxazepin-5(6H)-one, 3-chloro-8,10-dimethylpyridazinobenzo[3,4-b][1,5]benzoxazepin-5(6H)-one and 3-chloro-8-nitro-11-propyl-pyridazino[3,4-b][1,5]benzodiazipin-5-one.

2. A compound according to claim 1 of the formula I, wherein $R^1$ and $R^2$ together with the carbon atoms, to which they are attached, form a fused, saturated or unsaturated 5- or 6-membered C-bound carbocyclic or heterocyclic ring comprising 1 heteroatom, selected from nitrogen, oxygen and sulfur as ring member and 0, 1 or 2 further heteroatoms, independently selected from O, S and N, as ring members, wherein the fused ring is unsubstituted or may carry 1, 2 or 3 substituents selected, independently of each other, from the group of radicals $R^4$ as defined in claim 1.

3. A compound according to claim 2 of the formula I, wherein $R^1$ and $R^2$ together with the carbon atoms, to which they are attached, form a fused benzene ring which is unsubstituted or may carry 1 or 2 substituents selected, independently of each other, from the group of radicals $R^4$ as defined in claim 1.

4. A compound according to claim 2 of the formula I, wherein $R^1$ and $R^2$ together with the carbon atoms, to which they are attached, form a fused heteroaromatic ring, selected from pyridine, thiophene and thiazole, the fused heteroaromatic being unsubstituted or carrying 1 or 2 substituents selected, independently of each other, from the group of radicals $R^4$ as defined in claim 1.

5. A compound according to claim 2, wherein $R^4$ is absent or $R^4$ is selected from the group of halogen, OH, CN, nitro, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, $C_3$-$C_7$-cycloalkyl, $C_1$-$C_6$-alkoxy, fluorinated $C_1$-$C_6$-alkoxy, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, carboxy, $C_1$-$C_6$-alkyloxycarbonyl, fluorinated $C_1$-$C_6$-alkoxycarbonyl, $NR^aR^b$, C(O)—$NR^eR^f$, NH—C(O)—$NR^eR^f$, $NR^aR^b$—$C_1$-$C_6$-alkylene, O—$NR^aR^b$, phenyl and a 5- or 6-membered C- or N-bound heteroaromatic radical comprising 1 nitrogen atom as ring member and 0, 1, 2 or 3 further heteroatoms independently selected from O, S and N, as ring members, wherein phenyl and the heteroaromatic radical are, independently of each other, unsubstituted or carry 1, 2 or 3 substituents selected, independently of each other, from the group of radicals $R^{4b}$.

6. A compound according to claim 1, wherein $R^3$ is selected from the group of hydrogen, halogen, OH, CN, nitro, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, $C_3$-$C_7$-cycloalkyl, $C_1$-$C_6$-alkoxy, fluorinated $C_1$-$C_6$-alkoxy, $C_1$-$C_6$-alkylthio, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, carboxy, $C_1$-$C_6$-alkyloxycarbonyl, fluorinated $C_1$-$C_6$-alkoxycarbonyl, $NR^aR^b$, C(O)—$NR^eR^f$, NH—C(O)—$NR^eR^f$, $NR^aR^b$—$C_1$-$C_6$-alkylene, O—$NR^aR^b$, phenyl and a 5- or 6-membered C- or N-bound heteroaromatic radical comprising 1 nitrogen atom as ring member and 0, 1, 2 or 3 further heteroatoms independently selected from O, S and N, as ring members, wherein phenyl and the heteroaromatic radical are, independently of each other, unsubstituted or carry 1, 2 or 3 substituents selected, independently of each other, from the group of radicals $R^{3b}$.

7. A compound according to claim 1, wherein X is a radical N—$R^5$.

8. A compound according to claim 7, wherein $R^5$ is hydrogen.

9. A compound according to claim 1 of the formula I-A,

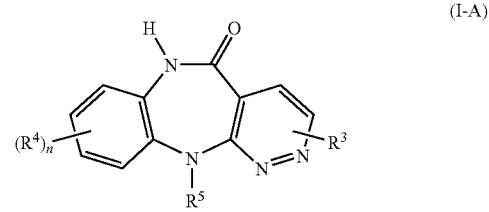

(I-A)

wherein n is 0 or 1 and wherein $R^3$, $R^4$ and $R^5$ are as defined above, and the physiologically tolerated acid addition salts thereof.

10. A compound according to claim 1, wherein X is O, NH or N—$C_1$-$C_4$-alkyl and wherein $R^1$ and $R^2$ are independently selected from the group consisting of H, $NH_2$, NH—$C_1$-$C_4$-alkyl, OH, O—$C_1$-$C_4$-alkyl, halogen, $C_2$-$C_4$-alkyl, $C_3$-$C_4$-cycloalkyl, $C_3$-$C_4$-alkenyl, fluorinated $C_1$-$C_4$-alkyl, fluorinated $C_3$-$C_4$-cycloalkyl, fluorinated $C_3$-$C_4$-alkenyl, formyl, $C_1$-$C_3$-alkylcarbonyl, and an aromatic radical Ar, which is selected from the group consisting of phenyl and a 5- or 6-membered C-bound heteroaromatic radical, wherein Ar carries 1 radical $R^{4x}$ which is selected from the group consisting of $C_2$-$C_6$-alkyl, $C_3$-$C_6$-cycloalkyl, $C_2$-$C_6$-alkoxy, fluorinated $C_2$-$C_6$-alkyl, fluorinated $C_3$-$C_6$-cycloalkyl, fluorinated $C_2$-$C_6$-alkoxy, $NR^eR^f$, 1-aziridinyl, azetidin-1-yl, pyrrolidin-1-yl, piperidin-1-yl and homopiperidin-1-yl, an optionally substituted phenyl group and an aromatic 5- or 6-membered C-bound heteroaromatic radical comprising 1 nitrogen atom as ring member and 0, 1, 2 or 3 further heteroatoms independently selected from O, S and N, wherein optional substituents comprise 1, 2, 3 or 4 radicals selected from H, halogen, cyano, $C_1$-$C_4$-alkyl and fluorinated $C_1$-$C_4$-alkyl; or, taken together, $R^1$ and $R^2$ form a fused, saturated or unsaturated 5-, 6- or 7-membered C-bound carbocyclic or heterocyclic ring which may carry 1, 2 or 3 substituents $R^{4x}$ as defined above; and $R^3$ has one of the meanings given for $R^1$.

11. A compound according to claim 10, wherein X is NH.

12. A compound according to claim 1 of the formula I-A'

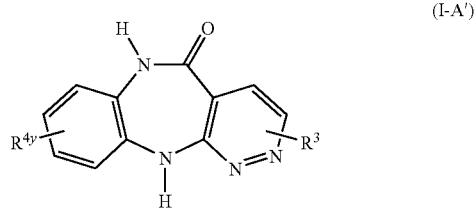

(I-A')

wherein $R^3$ and $R^{4y}$ are independently selected from the group consisting of H, $NH_2$, NH—$C_1$-$C_4$-alkyl, OH, O—$C_1$-$C_4$-alkyl, halogen, $C_2$-$C_4$-alkyl, $C_3$-$C_4$-cycloalkyl, $C_3$-$C_4$-alkenyl, fluorinated $C_1$-$C_4$-alkyl, fluorinated $C_3$-$C_4$-cycloalkyl, fluorinated $C_3$-$C_4$-alkenyl, formyl, $C_1$-$C_3$-alkylcarbonyl, and an aromatic radical Ar, which is selected from the group consisting of phenyl and a 5- or 6-membered C-bound heteroaromatic radical, wherein Ar carries 1 radical $R^y$ which is selected from the group consisting of $C_2$-$C_6$-alkyl, $C_3$-$C_6$-cycloalkyl, $C_2$-$C_6$-alkoxy, fluorinated $C_2$-$C_6$-alkyl, fluorinated $C_3$-$C_6$-cycloalkyl, fluorinated $C_2$-$C_6$-alkoxy, $NR^eR^f$, 1-aziridinyl, azetidin-1-yl, pyrrolidin-1-yl, piperidin-1-yl and homopiperidin-1-yl, an optionally substituted phenyl group and an aromatic 5- or 6-membered C-bound heteroaromatic radical comprising 1 nitrogen atom as ring member and 0, 1, 2 or 3 further heteroatoms independently selected from O, S and N, wherein optional substituents comprise 1, 2, 3 or 4 radicals selected from H, halogen, cyano, $C_1$-$C_4$-alkyl and fluorinated $C_1$-$C_4$-alkyl; and the physiologically tolerated acid addition salts thereof.

13. A compound according to claim 1, selected from 2-Chloro-11-oxo-10,11-dihydro-5H-3,4,5,10-tetraaza-dibenzo[a,d]cycloheptene-6-carboxylic acid amide, 2-Chloro-5,10-dihydro-3,4,5,10-tetraaza-dibenzo[a,d]cyclohepten-11-one, 5,10-Dihydro-3,4,5,10-tetraaza-dibenzo[a,d]cyclohepten-11-one, 2-Chloro-8-nitro-5,10-dihydro-3,4,5,10-tetraaza-dibenzo[a,d]cyclohepten-11-one, 2-Chloro-5,10-dihydro-3,4,5,6,10-pentaaza-dibenzo[a,d]cyclohepten-11-one and the physiologically tolerated acid addition salts thereof.

14. A compound according to claim 1, selected from 2-Chloro-5,10-dihydro-3,4,5,9,10-pentaaza-dibenzo[a,d]cyclohepten-11-one, 2-Bromo-5,10-dihydro-3,4,5,10-tetraaza-dibenzo[a,d]cyclohepten-11-one, 2-Iodo-5,10-dihydro-3,4,5,10-tetraaza-dibenzo[a,d]cyclohepten-11-one, 2-Vinyl-5,10-dihydro-3,4,5,10-tetraaza-dibenzo[a,d]cyclohepten-11-one, 2-Ethyl-5,10-dihydro-3,4,5,10-tetraaza-dibenzo[a,d]cyclohepten-11-one and the physiologically tolerated acid addition salts thereof.

15. A compound according to claim 1, selected from 2-Chloro-7-(azetidin-1-yl)-5,10-dihydro-3,4,5,10-tetraaza-dibenzo[a,d]cyclohepten-11-one, 2-Chloro-7-(pyrrolidin-1-yl)-5,10-dihydro-3,4,5,10-tetraaza-dibenzo[a,d]-cyclohepten-11-one, 2-Chloro-7-(piperidin-1-yl)-5,10-dihydro-3,4,5,10-tetraaza-dibenzo[a,d]cyclohepten-11-one, 2-Chloro-7-(piperazin-1-yl)-5,10-dihydro-3,4,5,10-tetraaza-dibenzo[a,d]-cyclohepten-11-one, 2-Chloro-7-(morpholin-4-yl)-5,10-dihydro-3,4,5,10-tetraaza-dibenzo[a,d]-cyclohepten-11-one, 2-Chloro-7-(homopiperidin-1-yl)-5,10-dihydro-3,4,5,10-tetraaza-dibenzo[a,d]-cyclohepten-11-one, and the physiologically tolerated acid addition salts thereof.

16. A pharmaceutical composition comprising at least one compound of claim 1 or a physiologically tolerated acid addition salt thereof, optionally together with at least one physiologically acceptable carrier or auxiliary substance.

\* \* \* \* \*